(12) United States Patent
Bardy

(10) Patent No.: US 7,070,562 B2
(45) Date of Patent: Jul. 4, 2006

(54) SYSTEM AND METHOD FOR PROVIDING TIERED PATIENT FEEDBACK FOR USE IN AUTOMATED PATIENT CARE

(75) Inventor: Gust H. Bardy, Seattle, WA (US)

(73) Assignee: Cardiac Intelligence Corporation, Seattle, WA (US)

( * ) Notice: Subject to any disclaimer, the term of this patent is extended or adjusted under 35 U.S.C. 154(b) by 0 days.

(21) Appl. No.: 10/422,495

(22) Filed: Apr. 23, 2003

(65) Prior Publication Data

US 2003/0195397 A1    Oct. 16, 2003

Related U.S. Application Data

(60) Division of application No. 09/860,977, filed on May 18, 2001, now Pat. No. 6,974,413, which is a continuation of application No. 09/476,602, filed on Dec. 31, 1999, now Pat. No. 6,270,457, which is a continuation-in-part of application No. 09/324,894, filed on Jun. 3, 1999, now Pat. No. 6,312,378.

(51) Int. Cl.
*A61B 5/04* (2006.01)

(52) U.S. Cl. .................................... 600/300

(58) Field of Classification Search ............ 600/300, 600/301, 309, 58, 513; 379/106.2; 128/903
See application file for complete search history.

(56) References Cited

U.S. PATENT DOCUMENTS

| | | | |
|---|---|---|---|
| 4,142,533 A | 3/1979 | Brownlee et al. |
| 4,531,527 A | 7/1985 | Reinhold, Jr. et al. |
| 4,686,999 A | 8/1987 | Snyder et al. |
| 4,809,697 A | 3/1989 | Causey, III et al. |
| 4,852,570 A | 8/1989 | Levine |
| 4,958,645 A | 9/1990 | Cadell et al. |
| 4,974,607 A | 12/1990 | Miwa |
| 4,987,897 A | 1/1991 | Funke |
| 5,040,536 A | 8/1991 | Riff |
| 5,113,859 A | 5/1992 | Funke |
| 5,113,869 A | 5/1992 | Nappholz et al. |
| 5,133,346 A | 7/1992 | Kulkarni |
| 5,199,428 A | 4/1993 | Obel et al. |
| 5,331,549 A | 7/1994 | Crawford, Jr. |
| 5,336,245 A | 8/1994 | Adams et al. |
| 5,355,889 A | 10/1994 | Nevo et al. |

(Continued)

FOREIGN PATENT DOCUMENTS

EP        0 34 2859        11/1989

(Continued)

OTHER PUBLICATIONS

Moody GB, "Integration of Real-Time and Off-Line Clinical Data in the MIMIC Database," Computers in Cardiology 1997 vol. 24, pp.585-588, Cambridge, MA USA.

(Continued)

*Primary Examiner*—Robert E. Pezzuto
*Assistant Examiner*—Frances P. Oropeza
(74) *Attorney, Agent, or Firm*—Patrick J. S. Inouye

(57) ABSTRACT

A system and method for providing tiered patient feedback for use in automated patient care is described. Physiological measures are analyzed. Each physiological measure is representative of at least one of measured and derived patient information recorded on a substantially continuous basis and was retrieved from one such patient care record to determine a patient status. Tiered feedback is provided to an individual patient responsive to the patient status.

11 Claims, 20 Drawing Sheets

U.S. PATENT DOCUMENTS

| | | | |
|---|---|---|---|
| 5,357,427 A | 10/1994 | Langen et al. | |
| 5,390,238 A | 2/1995 | Kirk et al. | |
| 5,416,695 A | 5/1995 | Stutman et al. | |
| 5,421,343 A | 6/1995 | Feng | |
| 5,437,278 A | 8/1995 | Wilk | |
| 5,438,983 A | 8/1995 | Falcone | |
| 5,464,012 A | 11/1995 | Falcone | |
| 5,544,661 A | 8/1996 | Davis et al. | |
| 5,553,609 A | 9/1996 | Chen et al. | |
| 5,576,952 A | 11/1996 | Stutman | |
| 5,591,215 A | 1/1997 | Greenhut et al. | |
| 5,603,331 A * | 2/1997 | Heemels et al. | 600/508 |
| 5,660,183 A | 8/1997 | Chiang et al. | |
| 5,687,734 A | 11/1997 | Dempsey et al. | |
| 5,697,959 A | 12/1997 | Poore | |
| 5,704,366 A | 1/1998 | Tracklind et al. | |
| 5,711,297 A | 1/1998 | Iliff | |
| 5,713,350 A | 2/1998 | Yokota et al. | |
| 5,720,770 A * | 2/1998 | Nappholz et al. | 607/30 |
| 5,720,771 A | 2/1998 | Snell | |
| 5,724,580 A | 3/1998 | Levi et al. | |
| 5,724,983 A | 3/1998 | Selker et al. | |
| 5,738,102 A | 4/1998 | Lemelson | |
| 5,743,267 A | 4/1998 | Nikolic | |
| 5,749,907 A | 5/1998 | Mann | |
| 5,749,908 A | 5/1998 | Snell | |
| 5,752,976 A | 5/1998 | Duffin et al. | |
| 5,769,074 A | 6/1998 | Barnhill et al. | |
| 5,772,586 A | 6/1998 | Heinonen et al. | |
| 5,772,604 A | 6/1998 | Langberg et al. | |
| 5,778,882 A | 7/1998 | Raymond et al. | |
| 5,785,650 A | 7/1998 | Akasaka et al. | |
| 5,792,062 A | 8/1998 | Poon et al. | |
| 5,855,593 A | 1/1999 | Olson et al. | |
| 5,876,353 A | 3/1999 | Riff | |
| 5,879,375 A | 3/1999 | Larson, Jr. et al. | |
| 5,891,178 A | 4/1999 | Mann et al. | |
| 5,897,493 A | 4/1999 | Brown | |
| 5,911,132 A | 6/1999 | Sloane | |
| 5,931,857 A | 8/1999 | Prieve | |
| 5,954,640 A | 9/1999 | Szabo | |
| 5,957,861 A | 9/1999 | Combs et al. | |
| 5,974,124 A | 10/1999 | Schlueter, Jr. et al. | |
| 5,987,352 A | 11/1999 | Klein et al. | |
| 6,024,699 A | 2/2000 | Surwit et al. | |
| 6,047,203 A | 4/2000 | Sackner et al. | |
| 6,050,940 A | 4/2000 | Braun | |
| 6,067,466 A | 5/2000 | Selker | |
| 6,073,046 A | 6/2000 | Patel | |
| 6,080,106 A | 6/2000 | Lloyd et al. | |
| 6,083,248 A | 7/2000 | Thompson | |
| 6,093,146 A | 7/2000 | Filangeri | |
| 6,095,985 A | 8/2000 | Raymond et al. | |
| 6,102,856 A | 8/2000 | Groff et al. | |
| 6,122,351 A | 9/2000 | Schlueter, Jr. et al. | |
| 6,139,494 A | 10/2000 | Cairnes | |
| 6,155,267 A | 12/2000 | Nelson | |
| 6,168,563 B1 | 1/2001 | Brown | |
| 6,168,653 B1 * | 1/2001 | Myers | 96/4 |
| 6,171,237 B1 | 1/2001 | Avitall et al. | |
| 6,171,256 B1 | 1/2001 | Joo et al. | |
| 6,223,078 B1 | 4/2001 | Marcovecchio | |
| 6,225,901 B1 | 5/2001 | Kail, IV | |
| 6,246,992 B1 | 6/2001 | Brown | |
| 6,249,705 B1 | 6/2001 | Snell | |
| 6,250,309 B1 | 6/2001 | Krichen et al. | |
| 6,263,245 B1 | 7/2001 | Snell | |
| 6,287,252 B1 | 9/2001 | Lugo | |
| 6,290,646 B1 * | 9/2001 | Cosentino et al. | 600/300 |
| 6,302,844 B1 | 10/2001 | Walker | |
| 6,336,900 B1 | 1/2002 | Alleckson | |
| 6,363,282 B1 | 3/2002 | Nichols et al. | |
| 6,416,471 B1 | 7/2002 | Kumar | |
| 6,442,433 B1 | 8/2002 | Linberg | |
| 6,454,705 B1 | 9/2002 | Cosentino et al. | |
| 6,477,424 B1 | 11/2002 | Thompson et al. | |
| 6,497,655 B1 | 12/2002 | Linberg et al. | |

FOREIGN PATENT DOCUMENTS

| | | |
|---|---|---|
| EP | 0 513 457 | 11/1992 |
| EP | 0 531 889 A2 | 3/1993 |
| EP | 0 711 531 A1 | 5/1996 |
| WO | WO 97/39792 | 10/1997 |
| WO | WO 98/01742 | 2/1998 |
| WO | WO 99/46718 | 9/1999 |

OTHER PUBLICATIONS

Long WJ, et al., "Differential Diagnosis Generation From A Causal Network With Probabilities," Computers in Cardiology, 1988, Proceedings, pp. 185-188, Washington DC, USA.

* cited by examiner

Patient 1

| Set 0 | | | | Set n-2 | Set n-1 | Set n |
|---|---|---|---|---|---|---|
| $X_0$ | • | • | • | $X_{n-2}$ | $X_{n-1}$ | $X_n$ |
| $Y_0$ | • | • | • | $Y_{n-2}$ | $Y_{n-1}$ | $Y_n$ |
| $Z_0$ | • | • | • | $Z_{n-2}$ | $Z_{n-1}$ | $Z_n$ |

*time →*

Patient 2

| Set 0 | | | | Set n-2 | Set n-1 | Set n |
|---|---|---|---|---|---|---|
| $X_{0'}$ | • | • | • | $X_{n-2'}$ | $X_{n-1'}$ | $X_{n'}$ |
| $Y_{0'}$ | • | • | • | $Y_{n-2'}$ | $Y_{n-1'}$ | $Y_{n'}$ |
| $Z_{0'}$ | • | • | • | $Z_{n-2'}$ | $Z_{n-1'}$ | $Z_{n'}$ |

*time →*

Patient 3

| Set 0 | | | | Set n-2 | Set n-1 | Set n |
|---|---|---|---|---|---|---|
| $X_{0''}$ | • | • | • | $X_{n-2''}$ | $X_{n-1''}$ | $X_{n''}$ |
| $Y_{0''}$ | • | • | • | $Y_{n-2''}$ | $Y_{n-1''}$ | $Y_{n''}$ |
| $Z_{0''}$ | • | • | • | $Z_{n-2''}$ | $Z_{n-1''}$ | $Z_{n''}$ |

*time →*

FIGURE 6

Patient 2

| Set 0 | | Set n-2 | Set n-1 | Set n |
|---|---|---|---|---|
| | | Site A | | |
| $X'_{0_A}$ | • • • | $X'_{n-2_A}$ | $X'_{n-1_A}$ | $X'_{n_A}$ |
| $Y'_{0_A}$ | • • • | $Y'_{n-2_A}$ | $Y'_{n-1_A}$ | $Y'_{n_A}$ |
| $Z'_{0_A}$ | • • • | $Z'_{n-2_A}$ | $Z'_{n-1_A}$ | $Z'_{n_A}$ |
| | | Site B | | |
| $X'_{0_B}$ | • • • | $X'_{n-2_B}$ | $X'_{n-1_B}$ | $X'_{n_B}$ |
| $Y'_{0_B}$ | • • • | $Y'_{n-2_B}$ | $Y'_{n-1_B}$ | $Y'_{n_B}$ |
| $Z'_{0_B}$ | • • • | $Z'_{n-2_B}$ | $Z'_{n-1_B}$ | $Z'_{n_B}$ | time →

Patient 3

| Set 0 | | Set n-2 | Set n-1 | Set n |
|---|---|---|---|---|
| | | Site A | | |
| $X''_{0_A}$ | • • • | $X''_{n-2_A}$ | $X''_{n-1_A}$ | $X''_{n_A}$ |
| $Y''_{0_A}$ | • • • | $Y''_{n-2_A}$ | $Y''_{n-1_A}$ | $Y''_{n_A}$ |
| $Z''_{0_A}$ | • • • | $Z''_{n-2_A}$ | $Z''_{n-1_A}$ | $Z''_{n_A}$ |
| | | Site D | | |
| $X''_{0_D}$ | • • • | $X''_{n-2_D}$ | $X''_{n-1_D}$ | $X''_{n_D}$ |
| $Y''_{0_D}$ | • • • | $Y''_{n-2_D}$ | $Y''_{n-1_D}$ | $Y''_{n_D}$ |
| $Z''_{0_D}$ | • • • | $Z''_{n-2_D}$ | $Z''_{n-1_D}$ | $Z''_{n_D}$ | time →

Patient 1

| Set 0 | | Set n-2 | Set n-1 | Set n |
|---|---|---|---|---|
| | | Site A | | |
| $X_{0_A}$ | • • • | $X_{n-2_A}$ | $X_{n-1_A}$ | $X_{n_A}$ |
| $Y_{0_A}$ | • • • | $Y_{n-2_A}$ | $Y_{n-1_A}$ | $Y_{n_A}$ |
| $Z_{0_A}$ | • • • | $Z_{n-2_A}$ | $Z_{n-1_A}$ | $Z_{n_A}$ |
| | | Site B | | |
| $X_{0_B}$ | • • • | $X_{n-2_B}$ | $X_{n-1_B}$ | $X_{n_B}$ |
| $Y_{0_B}$ | • • • | $Y_{n-2_B}$ | $Y_{n-1_B}$ | $Y_{n_B}$ |
| $Z_{0_B}$ | • • • | $Z_{n-2_B}$ | $Z_{n-1_B}$ | $Z_{n_B}$ |
| | | Site C | | |
| $X_{0_C}$ | • • • | $X_{n-2_C}$ | $X_{n-1_C}$ | $X_{n_C}$ |
| $Y_{0_C}$ | • • • | $Y_{n-2_C}$ | $Y_{n-1_C}$ | $Y_{n_C}$ |
| $Z_{0_C}$ | • • • | $Z_{n-2_C}$ | $Z_{n-1_C}$ | $Z_{n_C}$ | time →

FIGURE 15

SYSTEM AND METHOD FOR PROVIDING TIERED PATIENT FEEDBACK FOR USE IN AUTOMATED PATIENT CARE

CROSS-REFERENCE TO RELATED APPLICATION

This patent application is a divisional of U.S. patent application Ser. No. 09/860,977, filed May 18, 2001, now U.S. Pat. No. 6,974,413; which is a continuation of Ser. No. 09/476,602, filed Dec. 31, 1999, now U.S. Pat. No. 6,270,457, issued Aug. 7, 2001; which is a continuation-in-part of Ser. No. 09/324,894, filed Jun. 3, 1999, now U.S. Pat. No. 6,312,378, issued Nov. 6, 2001, the disclosures of which are incorporated by reference.

FIELD OF THE INVENTION

The present invention relates in general to automated data collection and analysis, and, in particular, to a system and method for providing tiered patient feedback for use in automated patient care.

BACKGROUND OF THE INVENTION

A broad class of medical subspecialties, including cardiology, endocrinology, hematology, neurology, gastroenterology, urology, ophthalmology, and otolaryngology, to name a few, rely on accurate and timely patient information for use in aiding health care providers in diagnosing and treating diseases and disorders. Often, proper medical diagnosis requires information on physiological events of short duration and sudden onset, yet these types of events are often occur infrequently and with little or no warning. Fortunately, such patient information can be obtained via external, implantable, cutaneous, subcutaneous, and manual medical devices, and combinations thereof. For example, in the area of cardiology, implantable pulse generators (IPGs) are commonly used to treat irregular heartbeats, known as arrhythmias. There are three basic types of IPGs. Cardiac pacemakers are used to manage bradycardia, an abnormally slow or irregular heartbeat. Bradycardia can cause symptoms such as fatigue, dizziness, and fainting. Implantable cardioverter defibrillators (ICDs) are used to treat tachycardia, heart rhythms that are abnormally fast and life threatening. Tachycardia can result in sudden cardiac death (SCD). Finally, implantable cardiovascular monitors and therapeutic devices are used to monitor and treat structural problems of the heart, such as congestive heart failure and rhythm problems.

Pacemakers and ICDs, as well as other types of implantable and external medical devices, are equipped with an on-board, volatile memory in which telemetered signals can be stored for later retrieval and analysis. In addition, a growing class of cardiac medical devices, including implantable heart failure monitors, implantable event monitors, cardiovascular monitors, and therapy devices, are being used to provide similar stored device information. These devices are able to store more than thirty minutes of per heartbeat data. Typically, the telemetered signals can provide patient device information recorded on a per heartbeat, binned average basis, or derived basis from, for example, atrial electrical activity, ventricular electrical activity, minute ventilation, patient activity score, cardiac output score, mixed venous oxygen score, cardiovascular pressure measures, time of day, and any interventions and the relative success of such interventions. In addition, many such devices can have multiple sensors, or several devices can work together, for monitoring different sites within a patient's body.

Presently, stored device information is retrieved using a proprietary interrogator or programmer, often during a clinic visit or following a device event. The volume of data retrieved from a single device interrogation "snapshot" can be large and proper interpretation and analysis can require significant physician time and detailed subspecialty knowledge, particularly by cardiologists and cardiac electrophysiologists. The sequential logging and analysis of regularly scheduled interrogations can create an opportunity for recognizing subtle and incremental changes in patient condition otherwise undetectable by inspection of a single "snapshot." However, present approaches to data interpretation and understanding and practical limitations on time and physician availability make such analysis impracticable.

A prior art system for collecting and analyzing pacemaker and ICD telemetered signals in a clinical or office setting is the Model 9790 Programmer, manufactured by Medtronic, Inc., Minneapolis, Minn. This programmer can be used to retrieve data, such as patient electrocardiogram and any measured physiological conditions, collected by the IPG for recordation, display and printing. The retrieved data is displayed in chronological order and analyzed by a physician. Comparable prior art systems are available from other IPG manufacturers, such as the Model 2901 Programmer Recorder Monitor, manufactured by Guidant Corporation, Indianapolis, Ind., which includes a removable floppy diskette mechanism for patient data storage. These prior art systems lack remote communications facilities and must be operated with the patient present. These systems present a limited analysis of the collected data based on a single device interrogation and lack the capability to recognize trends in the data spanning multiple episodes over time or relative to a disease specific peer group.

A prior art system for locating and communicating with a remote medical device implanted in an ambulatory patient is disclosed in U.S. Pat. No. 5,752,976 ('976). The implanted device includes a telemetry transceiver for communicating data and operating instructions between the implanted device and an external patient communications device. The communications device includes a communication link to a remote medical support network, a global positioning satellite receiver, and a patient activated link for permitting patient initiated communication with the medical support network.

Related prior art systems for remotely communicating with and receiving telemetered signals from a medical device are disclosed in U.S. Pat. Nos. 5,113,869 ('869) and 5,336,245 ('245). In the '869 patent, an implanted AECG monitor can be automatically interrogated at preset times of day to telemeter out accumulated data to a telephonic communicator or a full disclosure recorder. The communicator can be automatically triggered to establish a telephonic communication link and transmit the accumulated data to an office or clinic through a modem. In the '245 patent, telemetered data is downloaded to a larger capacity, external data recorder and is forwarded to a clinic using an autodialer and fax modem operating in a personal computer-based programmer/interrogator. However, the '976 telemetry transceiver, '869 communicator, and '245 programmer/interrogator are limited to facilitating communication and transferal of downloaded patient data and do not include an ability to automatically track, recognize, and analyze trends in the data itself.

In addition, the uses of multiple sensors situated within a patient's body at multiple sites are disclosed in U.S. Pat. No.

5,040,536 ('536) and U.S. Pat. No. 5,987,352 ('352). In the '536 patent, an intravascular pressure posture detector includes at least two pressure sensors implanted in different places in the cardiovascular system, such that differences in pressure with changes in posture are differentially measurable. However, the physiological measurements are used locally within the device, or in conjunction with any implantable device, to effect a therapeutic treatment. In the '352 patent, an event monitor can include additional sensors for monitoring and recording physiological signals during arrhythmia and syncopal events. The recorded signals can be used for diagnosis, research or therapeutic study, although no systematic approach to analyzing these signals, particularly with respect to peer and general population groups, is presented.

Thus, there is a need for a system and method for providing continuous retrieval, transferal, and automated analysis of retrieved medical device information, such as telemetered signals, retrieved in general from a broad class of implantable and external medical devices. Preferably, the automated analysis would include recognizing a trend indicating disease onset, progression, regression, and status quo and determining whether medical intervention is necessary.

There is a further need for a system and method that would allow consideration of sets of collected measures, both actual and derived, from multiple device interrogations. These collected measures sets could then be compared and analyzed against short and long term periods of observation.

There is a further need for a system and method that would enable the measures sets for an individual patient to be self-referenced and cross-referenced to similar or dissimilar patients and to the general patient population. Preferably, the historical collected measures sets of an individual patient could be compared and analyzed against those of other patients in general or of a disease specific peer group in particular.

SUMMARY OF THE INVENTION

The present invention provides a system and method for automated collection and analysis of patient information retrieved from an implantable medical device for remote patient care. The patient device information relates to individual measures recorded by and retrieved from implantable medical devices, such as IPGs and monitors. The patient device information is received on a regular, e.g., daily, basis as sets of collected measures which are stored along with other patient records in a database. The information can be analyzed in an automated fashion and feedback provided to the patient at any time and in any location.

An embodiment of the present invention is a system and method for analyzing patient information for use in automated patient care. One or more physiological measures relating to individual patient information recorded on a substantially continuous basis are retrieved from a patient care record. The physiological measures retrieved from one such patient care record are analyzed to determine a patient status. Each physiological measure is representative of at least one of measured and derived patient information.

A further embodiment is a system and method for collecting physiological measures for use in automated patient care. One or more physiological measures relating to individual patient information are obtained from a medical device having a sensor for monitoring and recording from an anatomical site at least one of directly and derivatively. The physiological measures are stored in patient care records.

A further embodiment is a system and method for providing tiered patient feedback for use in automated patient care. Physiological measures are retrieved from one such patient care record are analyzed to determine a patient status. Each physiological measure is representative of at least one of measured and derived patient information recorded on a substantially continuous basis. Tiered feedback is provided to an individual patient responsive to the patient status.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 6 is a record view showing, by way of example, a set of partial cardiac patient care records stored in the database of the system of FIG. 1;

FIG. 15 is a record view showing, by way of example, a set of partial cardiac patient care records stored in the database of the system of FIG. 12;

DETAILED DESCRIPTION

Figure 1:
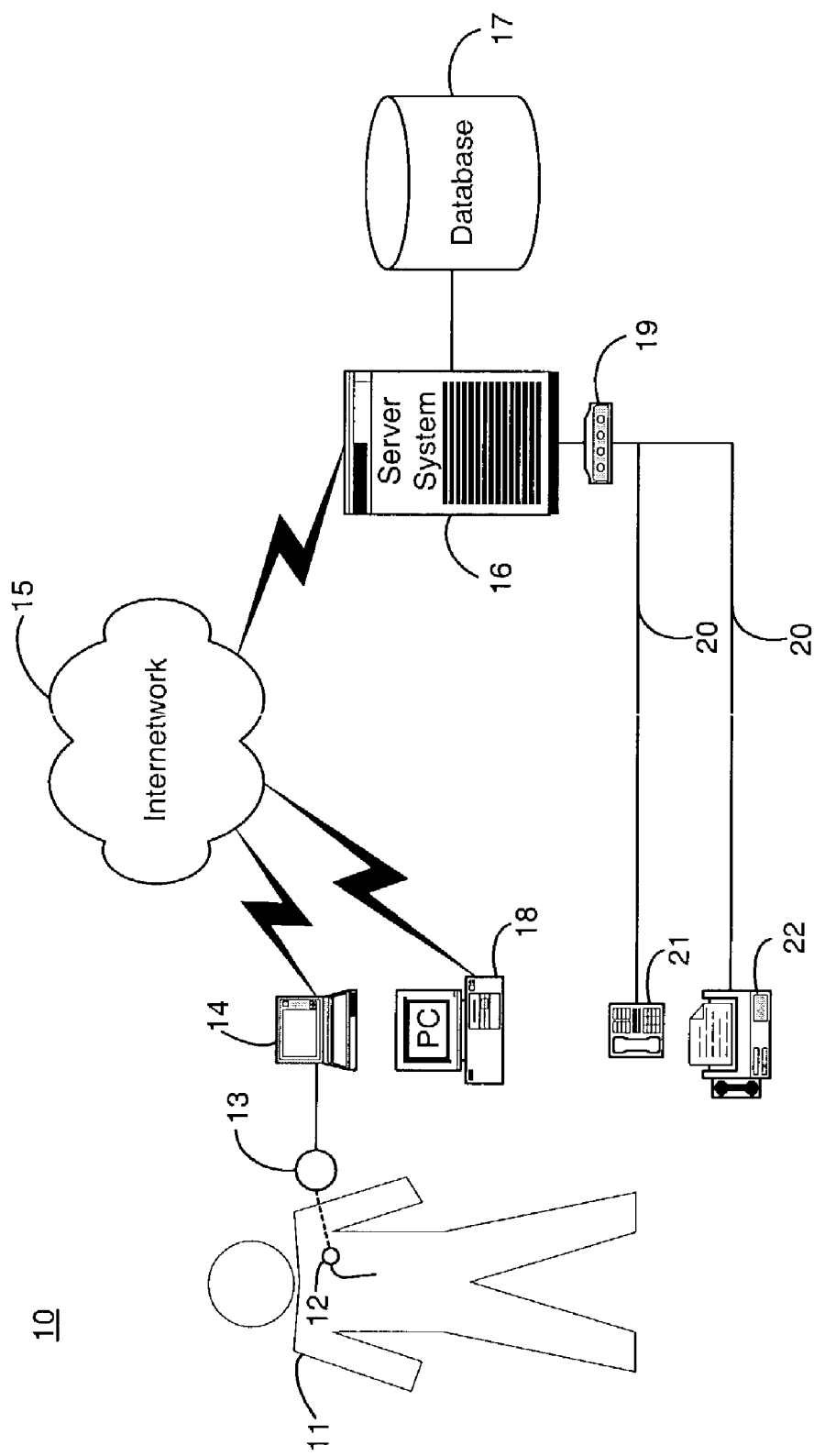
FIG. 1 is a block diagram showing a system for automated collection and analysis of patient information retrieved from an implantable medical device for remote patient care in accordance with the present invention.

FIG. 1 is a block diagram showing a system 10 for automated collection and analysis of patient information retrieved from an implantable medical device for remote patient care in accordance with the present invention. A patient 11 is a recipient of an implantable medical device 12, such as, by way of example, an IPG or a heart failure or event monitor, with a set of leads extending into his or her heart. The implantable medical device 12 includes circuitry for recording into a short-term, volatile memory telemetered signals, which are stored as a set of collected measures for later retrieval.

For an exemplary cardiac implantable medical device, the telemetered signals non-exclusively present patient information relating to: atrial electrical activity, ventricular electrical activity, time of day, activity level, cardiac output, oxygen level, cardiovascular pressure measures, the number and types of interventions made, and the relative success of any interventions made on a per heartbeat or binned average basis, plus the status of the batteries and programmed settings. Examples of pacemakers suitable for use in the present invention include the Discovery line of pacemakers, manufactured by Guidant Corporation, Indianapolis, Ind. Examples of ICDs suitable for use in the present invention include the Ventak line of ICDs, also manufactured by Guidant Corporation, Indianapolis, Ind.

In the described embodiment, the patient 11 has a cardiac implantable medical device. However, a wide range of related implantable medical devices are used in other areas of medicine and a growing number of these devices are also capable of measuring and recording patient information for later retrieval. These implantable medical devices include monitoring and therapeutic devices for use in metabolism, endocrinology, hematology, neurology, muscularology, gastro-intestinalogy, genital-urology, ocular, auditory, and similar medical subspecialties. One skilled in the art would readily recognize the applicability of the present invention to these related implantable medical devices.

On a regular basis, the telemetered signals stored in the implantable medical device 12 are retrieved. By way of example, a programmer 14 can be used to retrieve the telemetered signals. However, any form of programmer, interrogator, recorder, monitor, or telemetered signals transceiver suitable for communicating with an implantable medical device 12 could be used, as is known in the art. In addition, a personal computer or digital data processor could be interfaced to the implantable medical device 12, either directly or via a telemetered signals transceiver configured to communicate with the implantable medical device 12.

Using the programmer 14, a magnetized reed switch (not shown) within the implantable medical device 12 closes in response to the placement of a wand 13 over the location of the implantable medical device 12. The programmer 14 communicates with the implantable medical device 12 via RF signals exchanged through the wand 14. Programming or interrogating instructions are sent to the implantable medical device 12 and the stored telemetered signals are downloaded into the programmer 14. Once downloaded, the telemetered signals are sent via an internetwork 15, such as the Internet, to a server system 16 which periodically receives and stores the telemetered signals in a database 17, as further described below with reference to FIG. 2.

An example of a programmer 14 suitable for use in the present invention is the Model 2901 Programmer Recorder Monitor, manufactured by Guidant Corporation, Indianapolis, Ind., which includes the capability to store retrieved telemetered signals on a proprietary removable floppy diskette. The telemetered signals could later be electronically transferred using a personal computer or similar processing device to the internetwork 15, as is known in the art.

Other alternate telemetered signals transfer means could also be employed. For instance, the stored telemetered signals could be retrieved from the implantable medical device 12 and electronically transferred to the internetwork 15 using the combination of a remote external programmer and analyzer and a remote telephonic communicator, such as described in U.S. Pat. No. 5,113,869, the disclosure of which is incorporated herein by reference. Similarly, the stored telemetered signals could be retrieved and remotely downloaded to the server system 16 using a world-wide patient location and data telemetry system, such as described in U.S. Pat. No. 5,752,976, the disclosure of which is incorporated herein by reference.

The received telemetered signals are analyzed by the server system 16, which generates a patient status indicator. The feedback is then provided back to the patient 11 through a variety of means. By way of example, the feedback can be sent as an electronic mail message generated automatically by the server system 16 for transmission over the internetwork 15. The electronic mail message is received by personal computer 18 (PC) situated for local access by the patient 11. Alternatively, the feedback can be sent through a telephone interface device 19 as an automated voice mail message to a telephone 21 or as an automated facsimile message to a facsimile machine 22, both also situated for local access by the patient 11. In addition to a personal computer 18, telephone 21, and facsimile machine 22, feedback could be sent to other related devices, including a network computer, wireless computer, personal data assistant, television, or digital data processor. Preferably, the feedback is provided in a tiered fashion, as further described below with reference to FIG. 3.

Figure 2:
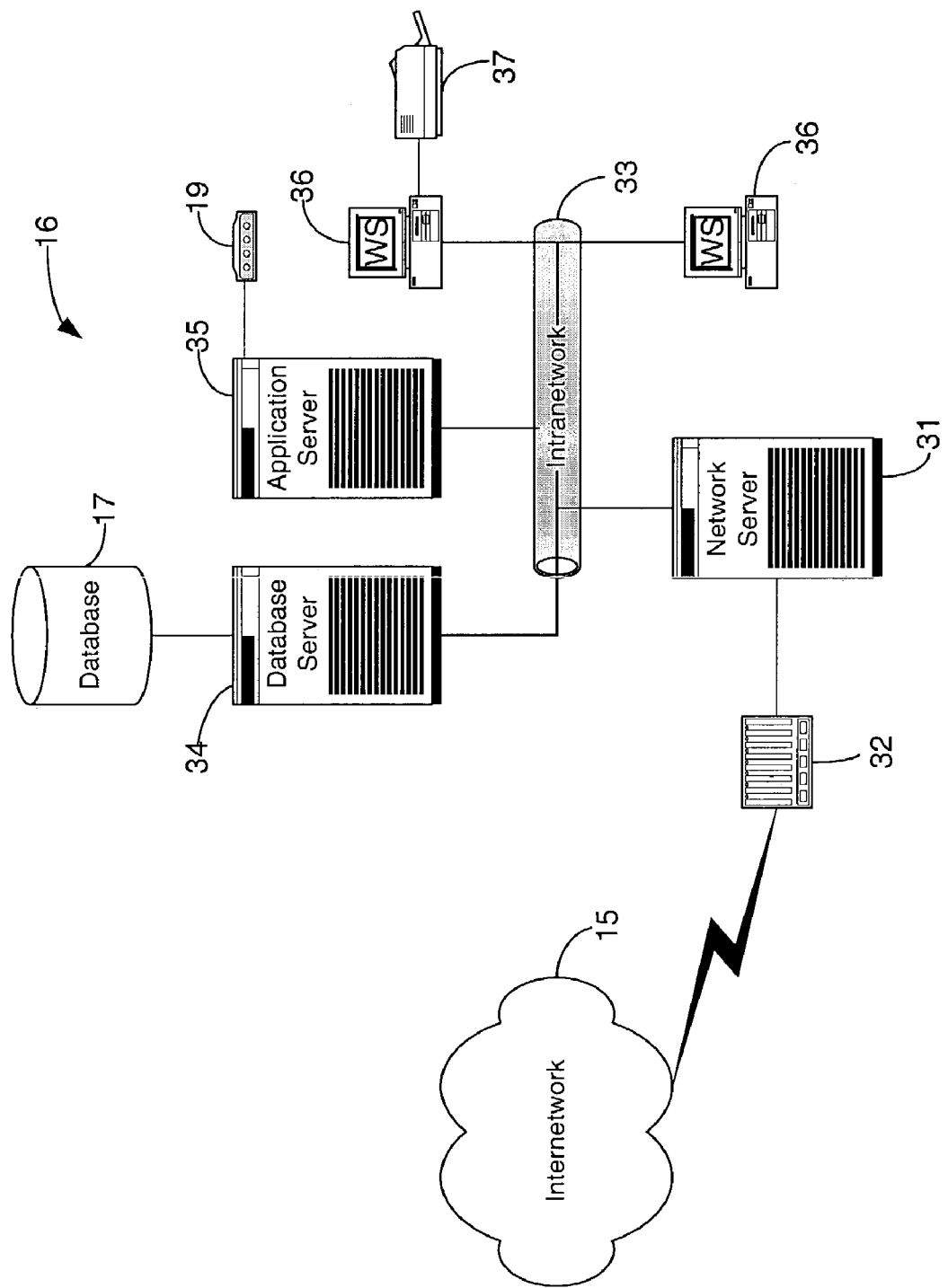
FIG. 2 is a block diagram showing the hardware components of the server system of the system of FIG. 1.

FIG. 2 is a block diagram showing the hardware components of the server system 16 of the system 10 of FIG. 1. The server system 16 consists of three individual servers: network server 31, database server 34, and application server 35. These servers are interconnected via an intranetwork 33. In the described embodiment, the functionality of the server system 16 is distributed among these three servers for efficiency and processing speed, although the functionality could also be performed by a single server or cluster of servers. The network server 31 is the primary interface of the server system 16 onto the internetwork 15. The network server 31 periodically receives the collected telemetered signals sent by remote implantable medical devices over the internetwork 15. The network server 31 is interfaced to the internetwork 15 through a router 32. To ensure reliable data exchange, the network server 31 implements a TCP/IP protocol stack, although other forms of network protocol stacks are suitable.

The database server 34 organizes the patient care records in the database 17 and provides storage of and access to information held in those records. A high volume of data in the form of collected measures sets from individual patients is received. The database server 34 frees the network server 31 from having to categorize and store the individual collected measures sets in the appropriate patient care record.

The application server 35 operates management applications and performs data analysis of the patient care records, as further described below with reference to FIG. 3. The application server 35 communicates feedback to the individual patients either through electronic mail sent back over the internetwork 15 via the network server 31 or as automated voice mail or facsimile messages through the telephone interface device 19.

The server system 16 also includes a plurality of individual workstations 36 (WS) interconnected to the intranetwork 33, some of which can include peripheral devices, such as a printer 37. The workstations 36 are for use by the data management and programming staff, nursing staff, office staff, and other consultants and authorized personnel.

The database 17 consists of a high-capacity storage medium configured to store individual patient care records and related health care information. Preferably, the database 17 is configured as a set of high-speed, high capacity hard drives, such as organized into a Redundant Array of Inexpensive Disks (RAID) volume. However, any form of volatile storage, non-volatile storage, removable storage, fixed storage, random access storage, sequential access storage, permanent storage, erasable storage, and the like would be equally suitable. The organization of the database 17 is further described below with reference to FIG. 3.

The individual servers and workstations are general purpose, programmed digital computing devices consisting of a central processing unit (CPU), random access memory (RAM), non-volatile secondary storage, such as a hard drive or CD ROM drive, network interfaces, and peripheral devices, including user interfacing means, such as a keyboard and display. Program code, including software programs, and data are loaded into the RAM for execution and processing by the CPU and results are generated for display, output, transmittal, or storage. In the described embodiment, the individual servers are Intel Pentium-based server systems, such as available from Dell Computers, Austin, Tex., or Compaq Computers, Houston, Tex. Each system is preferably equipped with 128 MB RAM, 100 GB hard drive capacity, data backup facilities, and related hardware for interconnection to the intranetwork 33 and internetwork 15. In addition, the workstations 36 are also Intel Pentium-based personal computer or workstation systems, also available from Dell Computers, Austin, Tex., or Compaq Computers, Houston, Tex. Each workstation is preferably equipped with 64 MB RAM, 10 GB hard drive capacity, and related hardware for interconnection to the intranetwork 33. Other types of server and workstation systems, including personal computers, minicomputers, mainframe computers, supercomputers, parallel computers, workstations, digital data processors and the like would be equally suitable, as is known in the art.

The telemetered signals are communicated over an internetwork 15, such as the Internet. However, any type of electronic communications link could be used, including an intranetwork link, serial link, data telephone link, satellite link, radio-frequency link, infrared link, fiber optic link, coaxial cable link, television link, and the like, as is known in the art. Also, the network server 31 is interfaced to the internetwork 15 using a T-1 network router 32, such as manufactured by Cisco Systems, Inc., San Jose, Calif. However, any type of interfacing device suitable for interconnecting a server to a network could be used, including a data modem, cable modem, network interface, serial connection, data port, hub, frame relay, digital PBX, and the like, as is known in the art.

Figure 3:
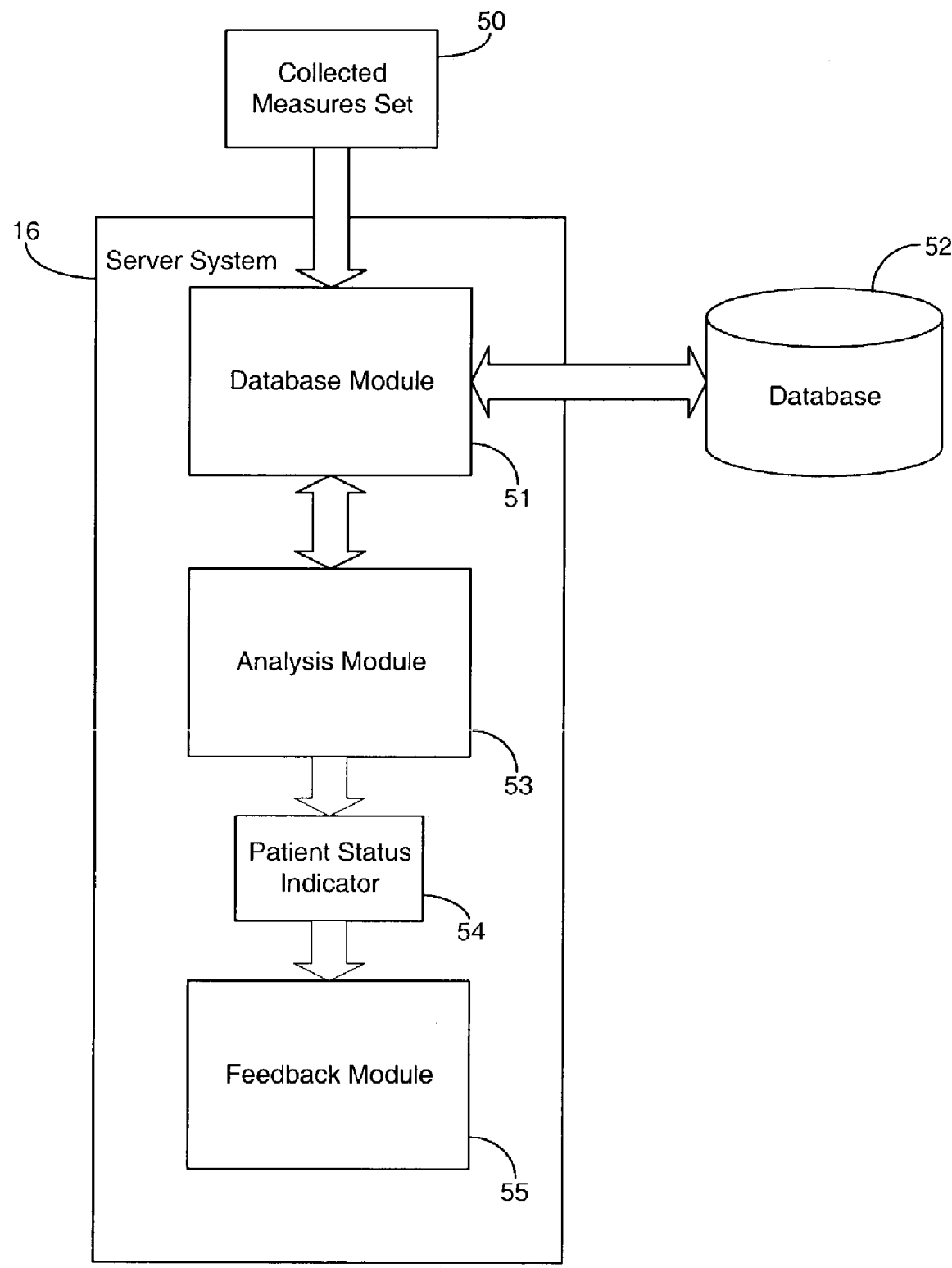
FIG. 3 is a block diagram showing the software modules of the server system of the system of FIG. 1.

FIG. 3 is a block diagram showing the software modules of the server system 16 of the system 10 of FIG. 1. Each module is a computer program written as source code in a conventional programming language, such as the C or Java programming languages, and is presented for execution by the CPU as object or byte code, as is known in the arts. The various implementations of the source code and object and byte codes can be held on a computer-readable storage medium or embodied on a transmission medium in a carrier wave. There are three basic software modules, which functionally define the primary operations performed by the server system 16: database module 51, analysis module 53, and feedback module 55. In the described embodiment, these modules are executed in a distributed computing environment, although a single server or a cluster of servers could also perform the functionality of the modules. The module functions are further described below in more detail beginning with reference to FIG. 7.

For each patient being provided remote patient care, the server system 16 periodically receives a collected measures set 50 which is forwarded to the database module 51 for processing. The database module 51 organizes the individual patient care records stored in the database 52 and provides the facilities for efficiently storing and accessing the collected measures sets 50 and patient data maintained in those records. An exemplary database schema for use in storing collected measures sets 50 in a patient care record is described below, by way of example, with reference to FIG. 4. The database server 34 (shown in FIG. 2) performs the functionality of the database module 51. Any type of database organization could be utilized, including a flat file system, hierarchical database, relational database, or distributed database, such as provided by database vendors, such as Oracle Corporation, Redwood Shores, Calif.

The analysis module 53 analyzes the collected measures sets 50 stored in the patient care records in the database 52. The analysis module 53 makes an automated determination of patient wellness in the form of a patient status indicator 54. Collected measures sets 50 are periodically received from implantable medical devices and maintained by the database module 51 in the database 52. Through the use of this collected information, the analysis module 53 can continuously follow the medical well being of a patient and can recognize any trends in the collected information that might warrant medical intervention. The analysis module 53 compares individual measures and derived measures obtained from both the care records for the individual patient and the care records for a disease specific group of patients or the patient population in general. The analytic operations performed by the analysis module 53 are further described below with reference to FIG. 4. The application server 35 (shown in FIG. 2) performs the functionality of the analysis module 53.

The feedback module 55 provides automated feedback to the individual patient based, in part, on the patient status indicator 54. As described above, the feedback could be by electronic mail or by automated voice mail or facsimile. Preferably, the feedback is provided in a tiered manner. In the described embodiment, four levels of automated feedback are provided. At a first level, an interpretation of the patient status indicator 54 is provided. At a second level, a notification of potential medical concern based on the patient status indicator 54 is provided. This feedback level could also be coupled with human contact by specially trained technicians or medical personnel. At a third level, the notification of potential medical concern is forwarded to medical practitioners located in the patient's geographic area. Finally, at a fourth level, a set of reprogramming instructions based on the patient status indicator 54 could be transmitted directly to the implantable medical device to modify the programming instructions contained therein. As is customary in the medical arts, the basic tiered feedback scheme would be modified in the event of bona fide medical emergency. The application server 35 (shown in FIG. 2) performs the functionality of the feedback module 55.

Figure 4:
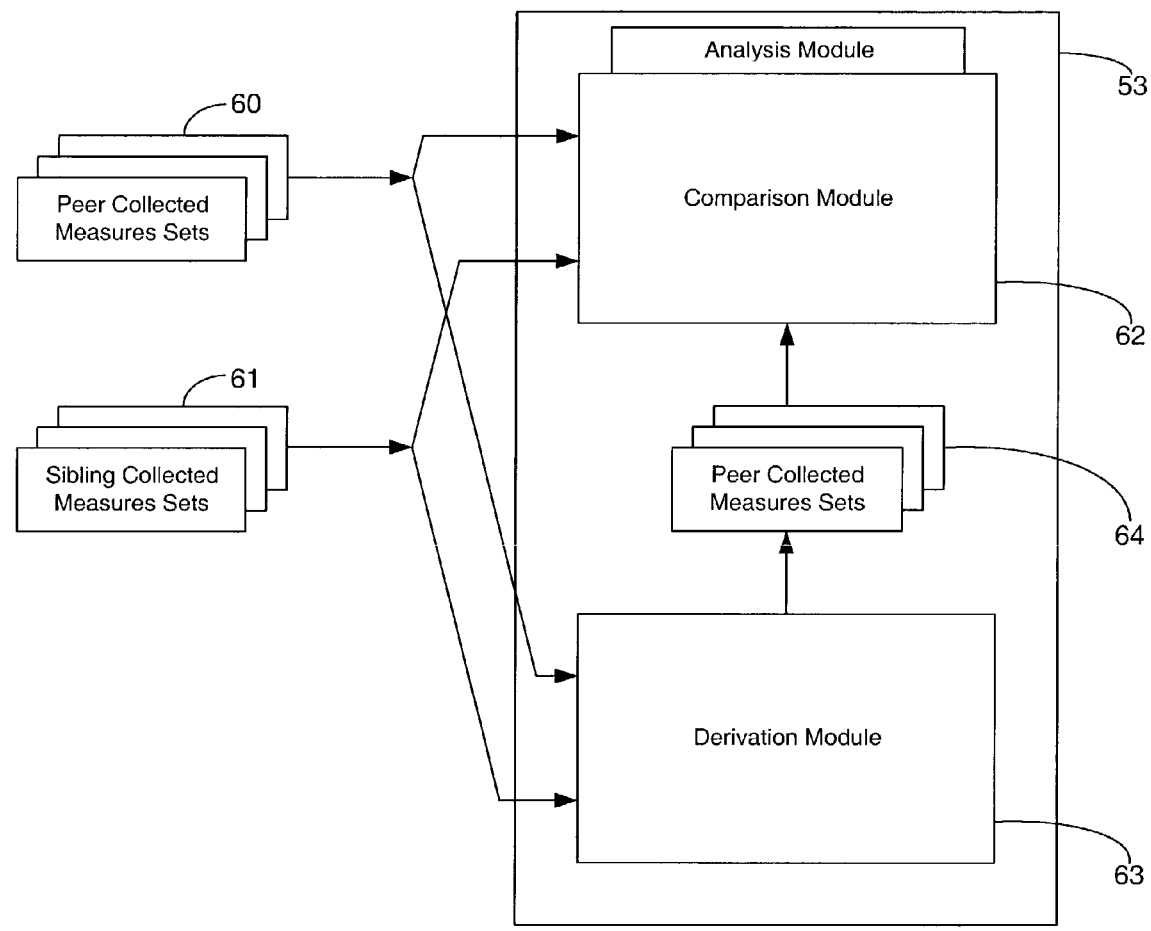
FIG. 4 is a block diagram showing the analysis module of the server system of FIG. 3.

FIG. 4 is a block diagram showing the analysis module 53 of the server system 16 of FIG. 3. The analysis module 53 contains two functional submodules: comparison module 62 and derivation module 63. The purpose of the comparison module 62 is to compare two or more individual measures, either collected or derived. The purpose of the derivation module 63 is to determine a derived measure based on one or more collected measures which is then used by the comparison module 62. For instance, a new and improved indicator of impending heart failure could be derived based on the exemplary cardiac collected measures set described with reference to FIG. 5. The analysis module 53 can operate either in a batch mode of operation wherein patient status indicators are generated for a set of individual patients or in a dynamic mode wherein a patient status indicator is generated on the fly for an individual patient.

The comparison module 62 receives as inputs from the database 17 two input sets functionally defined as peer collected measures sets 60 and sibling collected measures sets 61, although in practice, the collected measures sets are stored on a per sampling basis. Peer collected measures sets 60 contain individual collected measures sets that all relate to the same type of patient information, for instance, atrial electrical activity, but which have been periodically collected over time. Sibling collected measures sets 61 contain individual collected measures sets that relate to different types of patient information, but which may have been collected at the same time or different times. In practice, the collected measures sets are not separately stored as "peer" and "sibling" measures. Rather, each individual patient care record stores multiple sets of sibling collected measures. The distinction between peer collected measures sets 60 and sibling collected measures sets 61 is further described below with reference to FIG. 6.

The derivation module 63 determines derived measures sets 64 on an as-needed basis in response to requests from the comparison module 62. The derived measures 64 are determined by performing linear and non-linear mathematical operations on selected peer measures 60 and sibling measures 61, as is known in the art.

Figure 5:
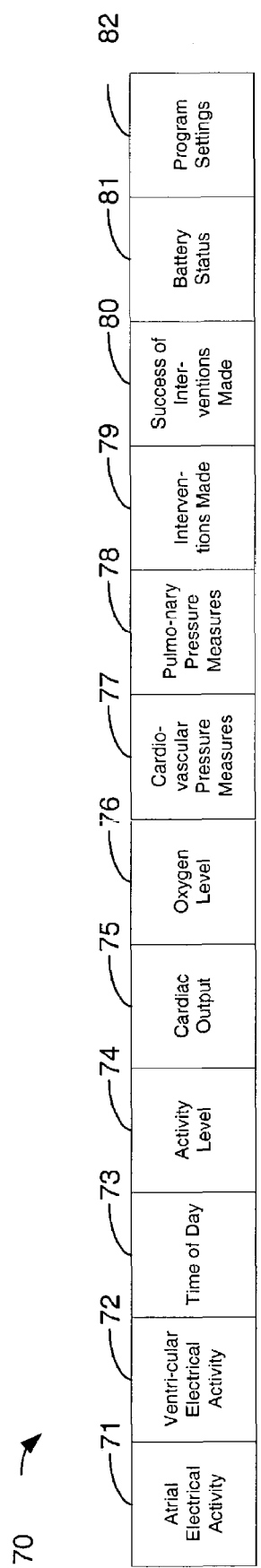
FIG. 5 is a database schema showing, by way of example, the organization of a cardiac patient care record stored in the database of the system of FIG. 1.

FIG. 5 is a database schema showing, by way of example, the organization of a cardiac patient care record stored 70 in the database 17 of the system 10 of FIG. 1. Only the information pertaining to collected measures sets are shown. Each patient care record would also contain normal identifying and treatment profile information, as well as medical history and other pertinent data (not shown). Each patient care record stores a multitude of collected measures sets for an individual patient. Each individual set represents a recorded snapshot of telemetered signals data which was recorded, for instance, per heartbeat or binned average basis by the implantable medical device 12. For example, for a cardiac patient, the following information would be recorded as a collected measures set: atrial electrical activity 71, ventricular electrical activity 72, time of day 73, activity level 74, cardiac output 15, oxygen level 76, cardiovascular pressure measures 77, pulmonary measures 78, interventions made by the implantable medical device 78, and the relative success of any interventions made 80. In addition, the implantable medical device 12 would also communicate device specific information, including battery status 81 and program settings 82. Other types of collected measures are possible. In addition, a well-documented set of derived measures can be determined based on the collected measures, as is known in the art.

FIG. 6 is a record view showing, by way of example, a set of partial cardiac patient care records stored in the database 17 of the system 10 of FIG. 1. Three patient care records are shown for Patient 1, Patient 2, and Patient 3. For each patient, three sets of measures are shown, X, Y and Z. The measures are organized into sets with Set 0 representing sibling measures made at a reference time t=0. Similarly, Set n−2, Set n−1 and Set n each represent sibling measures made at later reference times t=n−2, t=n−1 and t=n, respectively.

For a given patient, for instance, Patient 1, all measures representing the same type of patient information, such as measure X, are peer measures. These are measures, which are monitored over time in a disease-matched peer group. All measures representing different types of patient information, such as measures X, Y, and Z, are sibling measures. These are measures which are also measured over time, but which might have medically significant meaning when compared to each other within a single set. Each of the measures, X, Y, and Z, could be either collected or derived measures.

The analysis module 53 (shown in FIG. 4) performs two basic forms of comparison. First, individual measures for a given patient can be compared to other individual measures for that same patient. These comparisons might be peer-to-peer measures projected over time, for instance, $X_n$, $X_{n-1}$, $X_{n-2}$, ... $X_0$, or sibling-to-sibling measures for a single snapshot, for instance, $X_n$, $Y_n$, and $Z_n$, or projected over time, for instance, $X_n$, $Y_n$, $Z_n$, $X_{n-1}$, $Y_{n-1}$, $Z_{n-1}$, $X_{n-2}$, $Y_{n-2}$, $Z_{n-2}$, ... $X_0$, $Y_0$, $Z_0$. Second, individual measures for a given patient can be compared to other individual measures for a group of other patients sharing the same disease-specific characteristics or to the patient population in general. Again, these comparisons might be peer-to-peer measures projected over time, for instance, $X_n$, $X_{n'}$, $X_{n''}$, $X_{n-1}$, $X_{n-1'}$, $X_{n-1''}$, $X_{n-2}$, $X_{n-2'}$, $X_{n-2''}$ ... $X_0$, $X_{0'}$, $X_{0''}$, or comparing the individual patient's measures to an average from the group. Similarly, these comparisons might be sibling-to-sibling measures for single snapshots, for instance, $X_n$, $X_{n'}$, $X_{n''}$, $Y_n$, $Y_{n'}$, $Y_{n''}$, and $Z_n$, $Z_{n'}$, $Z_{n''}$, or projected over time, for instance $X_n$, $X_{n'}$, $X_{n''}$, $Y_n$, $Y_{n'}$, $Y_{n''}$, $Z_n$, $Z_{n'}$, $Z_{n''}$, $X_{n-1}$, $X_{n-1'}$, $X_{n-1''}$, $Y_{n-1}$, $Y_{n-1'}$, $Y_{n-1''}$, $Z_{n-1}$, $Z_{n-1'}$, $Z_{n-1''}$, $X_{n-2}$, $X_{n-2'}$, $X_{n-2''}$, $Y_{n-1}$, $Y_{n-1'}$, $Y_{n-1''}$, $Z_{n-1}$, $Z_{n-1'}$, $Z_{n-1''}$ ... $X_0$, $X_{0'}$, $X_{0''}$, $Y_0$, $Y_{0'}$, $Y_{0''}$, and $Z_0$, $Z_{0'}$, $Z_{0''}$. Other forms of comparisons are feasible.

Figure 7:
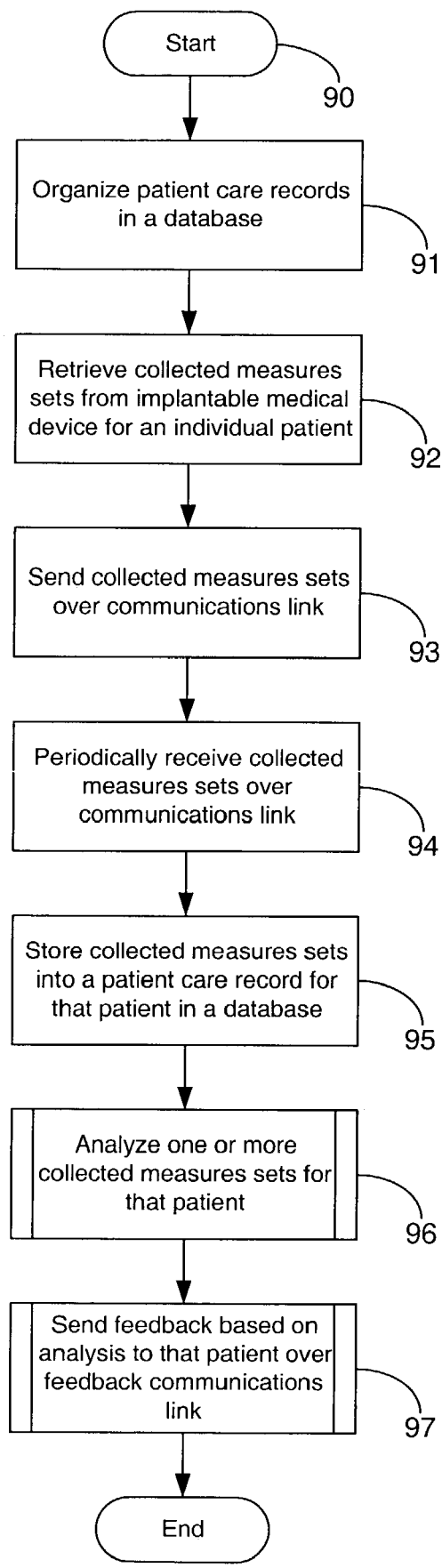
FIG. 7 is a flow diagram showing a method for automated collection and analysis of patient information retrieved from an implantable medical device for remote patient care in accordance with the present invention.

FIG. 7 is a flow diagram showing a method 90 for automated collection and analysis of patient information retrieved from an implantable medical device 12 for remote patient care in accordance with the present invention. The method 90 is implemented as a conventional computer program for execution by the server system 16 (shown in FIG. 1). As a preparatory step, the patient care records are organized in the database 17 with a unique patient care record assigned to each individual patient (block 91). Next, the collected measures sets for an individual patient are retrieved from the implantable medical device 12 (block 92) using a programmer, interrogator, telemetered signals transceiver, and the like. The retrieved collected measures sets are sent, on a substantially regular basis, over the internetwork 15 or similar communications link (block 93) and periodically received by the server system 16 (block 94). The collected measures sets are stored into the patient care record in the database 17 for that individual patient (block 95). One or more of the collected measures sets for that patient are analyzed (block 96), as further described below with reference to FIG. 8. Finally, feedback based on the analysis is sent to that patient over the internetwork 15 as an email message, via telephone line as an automated voice mail or facsimile message, or by similar feedback communications link (block 97), as further described below with reference to FIG. 11.

Figure 8:
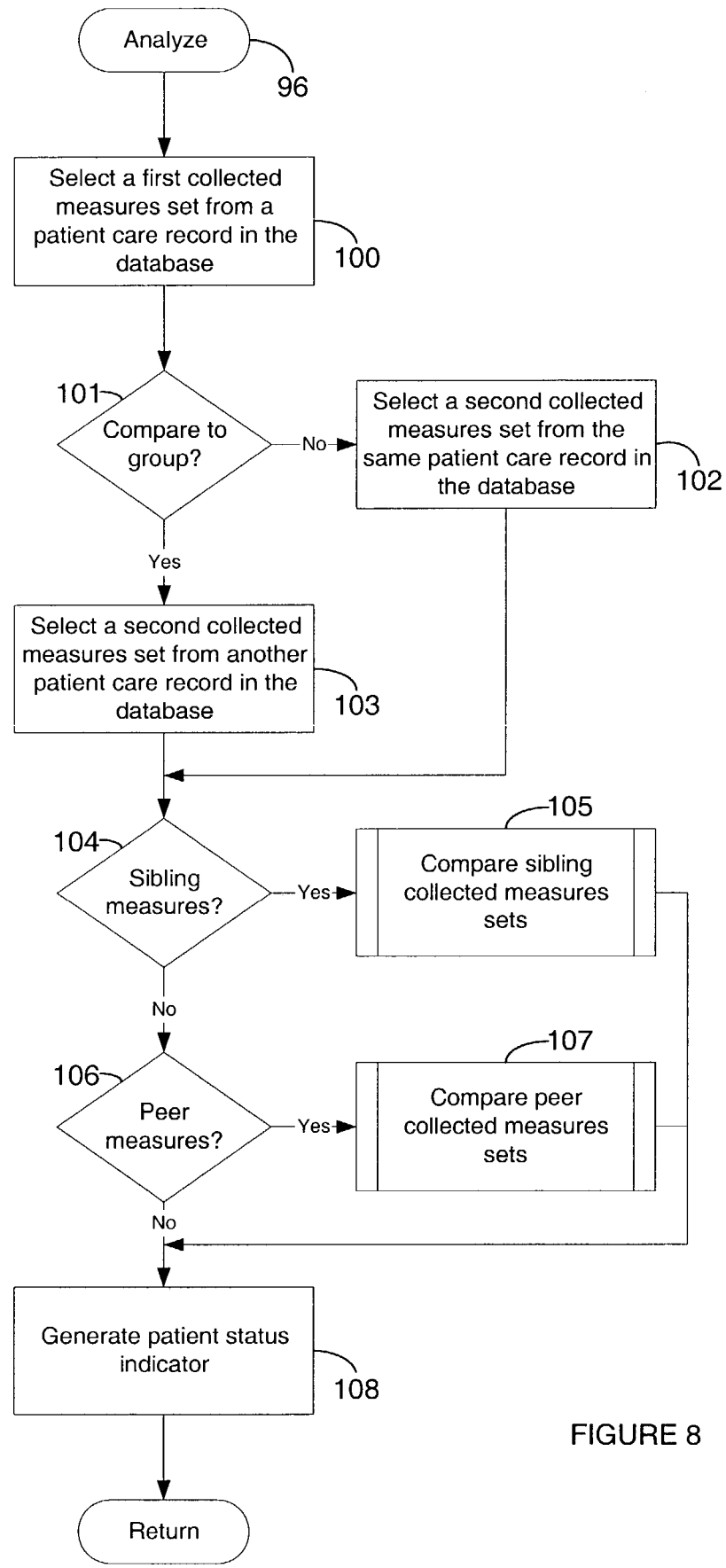
FIG. 8 is a flow diagram showing a routine for analyzing collected measures sets for use in the method of FIG. 7.

FIG. 8 is a flow diagram showing the routine for analyzing collected measures sets 96 for use in the method of FIG. 7. The purpose of this routine is to make a determination of general patient wellness based on comparisons and heuristic trends analyses of the measures, both collected and derived, in the patient care records in the database 17. A first collected measures set is selected from a patient care record in the database 17 (block 100). If the measures comparison is to be made to other measures originating from the patient care record for the same individual patient (block 101), a second collected measures set is selected from that patient care record (block 102). Otherwise, a group measures comparison is being made (block 101) and a second collected measures set is selected from another patient care record in the database 17 (block 103). Note the second collected measures set could also contain averaged measures for a group of disease specific patients or for the patient population in general.

Next, if a sibling measures comparison is to be made (block 104), a routine for comparing sibling collected measures sets is performed (block 105), as further described below with reference to FIG. 9. Similarly, if a peer measures comparison is to be made (block 106), a routine for comparing sibling collected measures sets is performed (block 107), as further described below with reference to FIGS. 10A and 10B.

Finally, a patient status indicator is generated (block 108). By way of example, cardiac output could ordinarily be approximately 5.0 liters per minute with a standard deviation of ±1.0. An actionable medical phenomenon could occur when the cardiac output of a patient is ±3.0–4.0 standard deviations out of the norm. A comparison of the cardiac output measures 75 (shown in FIG. 5) for an individual patient against previous cardiac output measures 75 would establish the presence of any type of downward health trend as to the particular patient. A comparison of the cardiac output measures 75 of the particular patient to the cardiac output measures 75 of a group of patients would establish whether the patient is trending out of the norm. From this type of analysis, the analysis module 53 generates a patient status indicator 54 and other metrics of patient wellness, as is known in the art.

Figure 9:
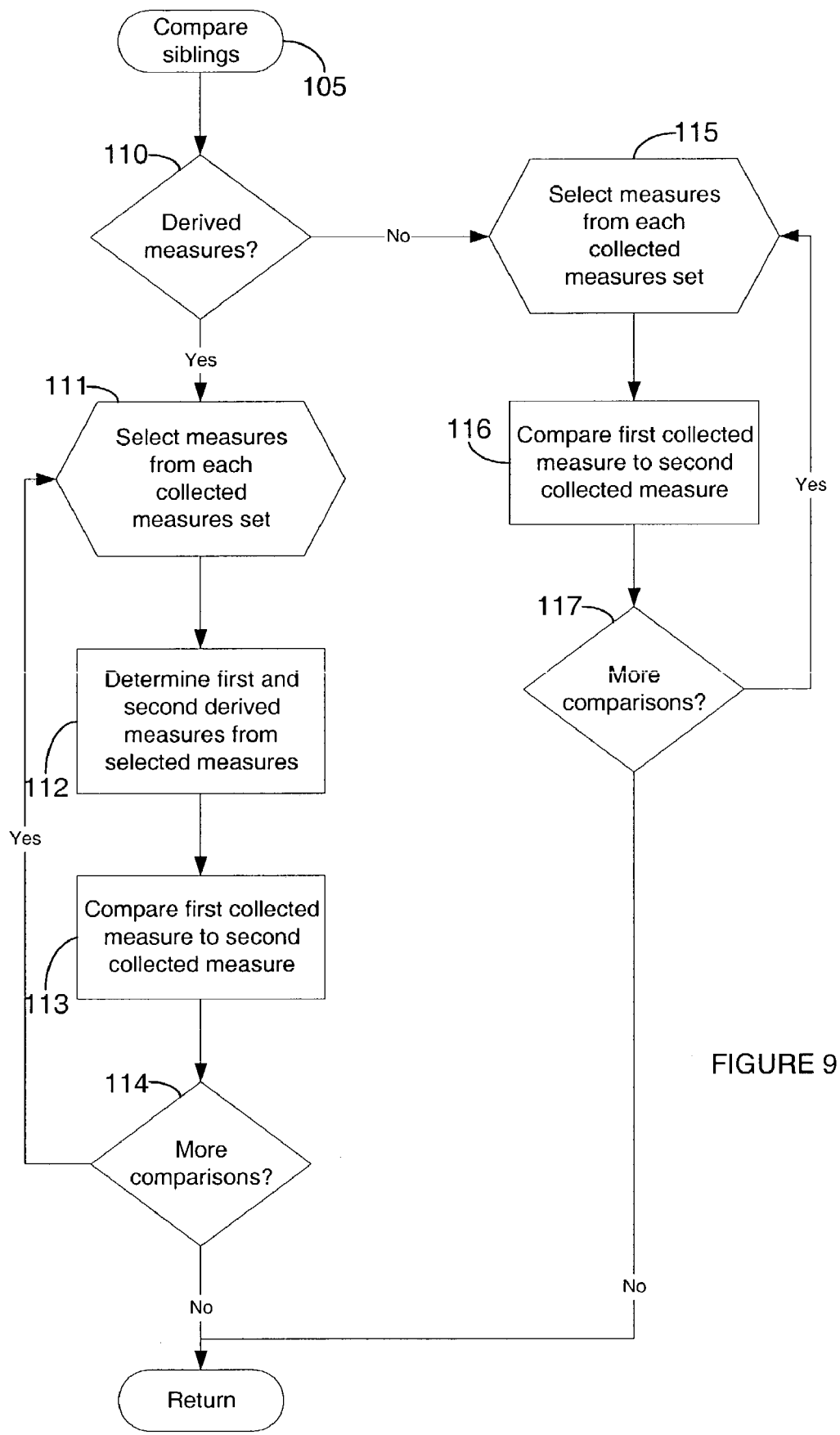
FIG. 9 is a flow diagram showing a routine for comparing sibling collected measures sets for use in the routine of FIG. 8.

FIG. 9 is a flow diagram showing the routine for comparing sibling collected measures sets 105 for use in the routine of FIG. 8. Sibling measures originate from the patient care records for an individual patient. The purpose of this routine is either to compare sibling derived measures to sibling derived measures (blocks 111–113) or sibling collected measures to sibling collected measures (blocks 115–117). Thus, if derived measures are being compared (block 110), measures are selected from each collected measures set (block 111). First and second derived measures are derived from the selected measures (block 112) using the derivation module 63 (shown in FIG. 4). The first and second derived measures are then compared (block 113) using the comparison module 62 (also shown in FIG. 4). The steps of selecting, determining, and comparing (blocks 111–113) are repeated until no further comparisons are required (block 114), whereupon the routine returns.

If collected measures are being compared (block 110), measures are selected from each collected measures set (block 115). The first and second collected measures are then compared (block 116) using the comparison module 62 (also shown in FIG. 4). The steps of selecting and comparing (blocks 115–116) are repeated until no further comparisons are required (block 117), whereupon the routine returns.

Figure 10A:
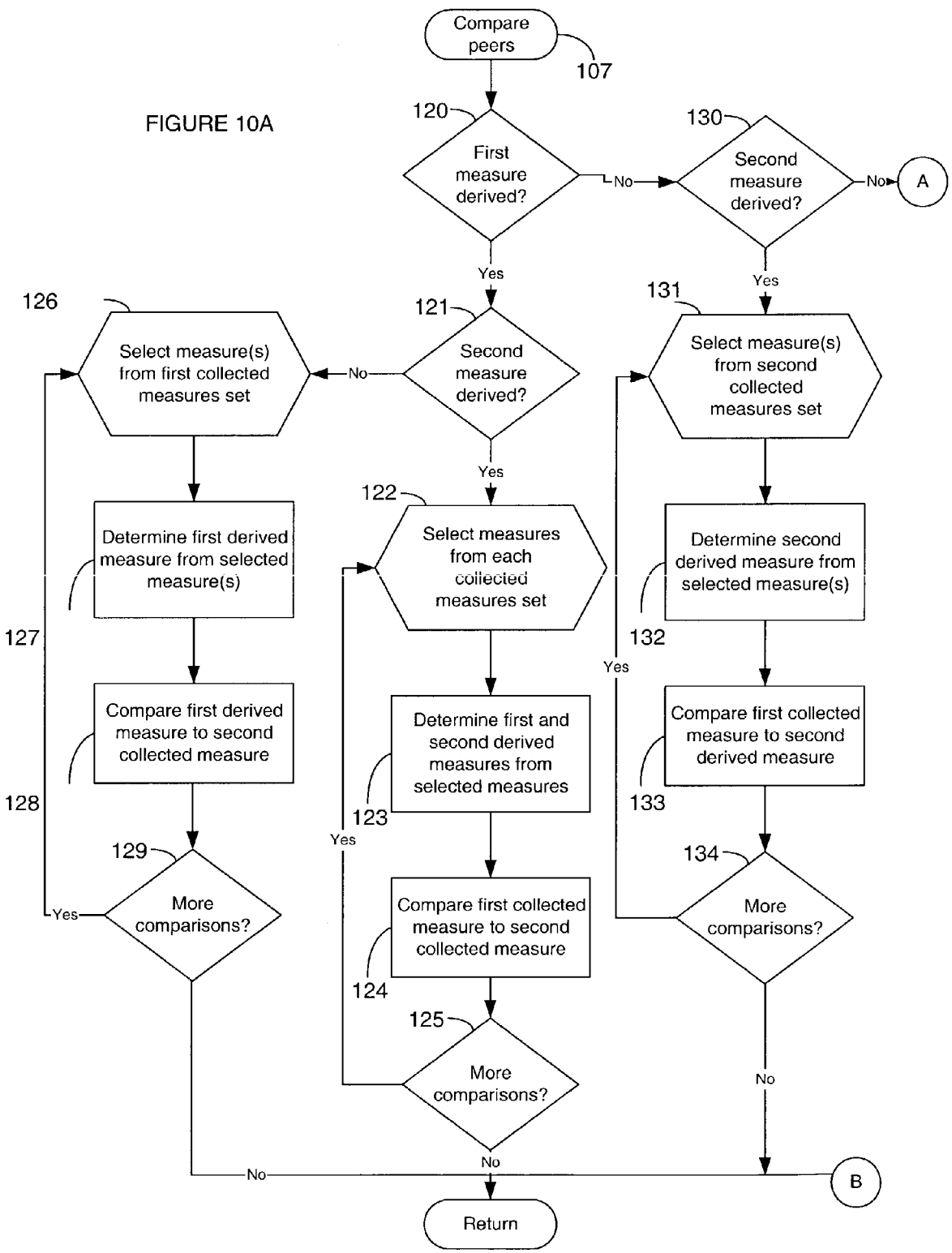
FIGS. 10A and 10B are flow diagrams showing a routine for comparing peer collected measures sets for use in the routine of FIG. 8.
Figure 10B:
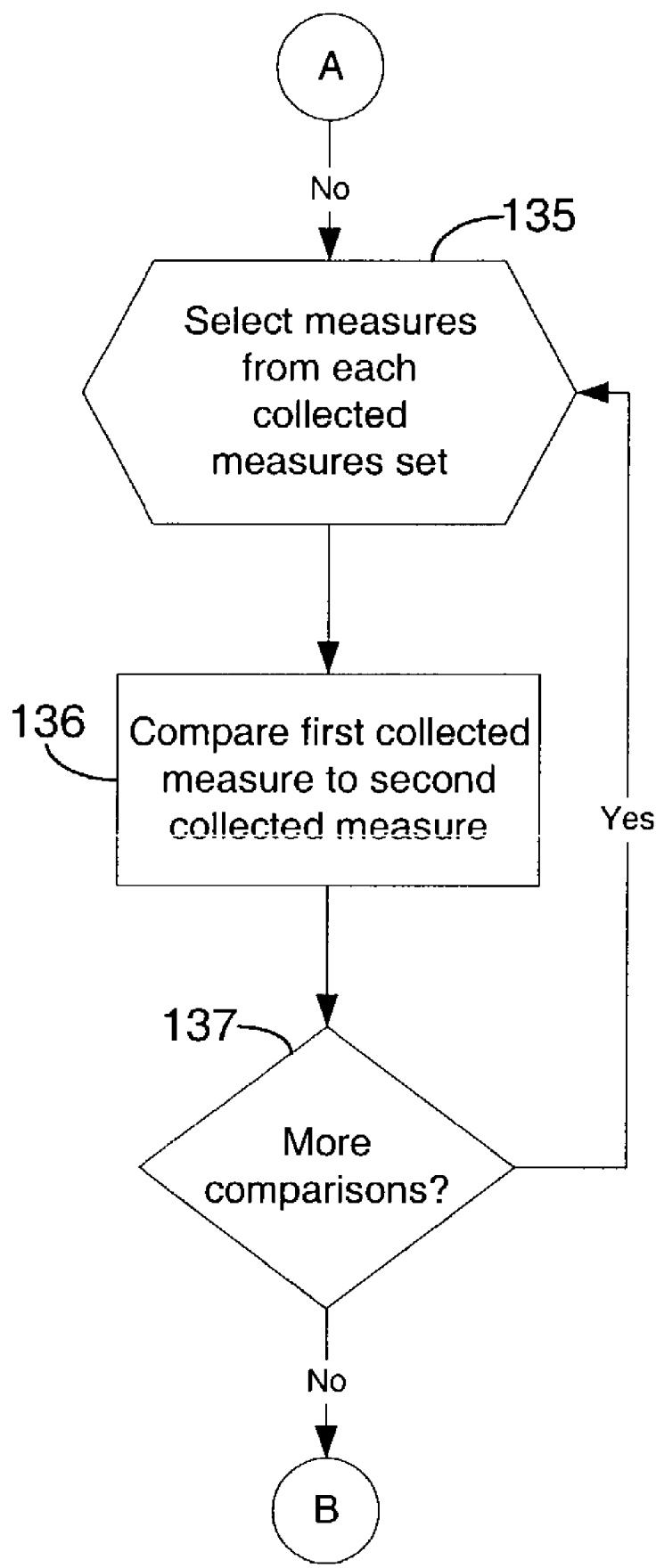

FIGS. 10A and 10B are a flow diagram showing the routine for comparing peer collected measures sets 107 for use in the routine of FIG. 8. Peer measures originate from patient care records for different patients, including groups of disease specific patients or the patient population in general. The purpose of this routine is to compare peer derived measures to peer derived measures (blocks 122–125), peer derived measures to peer collected measures (blocks 126–129), peer collected measures to peer derived measures (block 131–134), or peer collected measures to peer collected measures (blocks 135–137). Thus, if the first measure being compared is a derived measure (block 120) and the second measure being compared is also a derived measure (block 121), measures are selected from each collected measures set (block 122). First and second derived measures are derived from the selected measures (block 123) using the derivation module 63 (shown in FIG. 4). The first and second derived measures are then compared (block 124) using the comparison module 62 (also shown in FIG. 4). The steps of selecting, determining, and comparing (blocks 122–124) are repeated until no further comparisons are required (block 115), whereupon the routine returns.

If the first measure being compared is a derived measure (block 120) but the second measure being compared is a collected measure (block 121), a first measure is selected from the first collected measures set (block 126). A first derived measure is derived from the first selected measure (block 127) using the derivation module 63 (shown in FIG. 4). The first derived and second collected measures are then compared (block 128) using the comparison module 62 (also shown in FIG. 4). The steps of selecting, determining, and comparing (blocks 126–128) are repeated until no further comparisons are required (block 129), whereupon the routine returns.

If the first measure being compared is a collected measure (block 120) but the second measure being compared is a derived measure (block 130), a second measure is selected from the second collected measures set (block 131). A second derived measure is derived from the second selected measure (block 132) using the derivation module 63 (shown in FIG. 4). The first collected and second derived measures are then compared (block 133) using the comparison module 62 (also shown in FIG. 4). The steps of selecting, determining, and comparing (blocks 131–133) are repeated until no further comparisons are required (block 134), whereupon the routine returns.

If the first measure being compared is a collected measure (block 120) and the second measure being compared is also a collected measure (block 130), measures are selected from each collected measures set (block 135). The first and second collected measures are then compared (block 136) using the comparison module 62 (also shown in FIG. 4). The steps of selecting and comparing (blocks 135–136) are repeated until no further comparisons are required (block 137), whereupon the routine returns.

Figure 11:
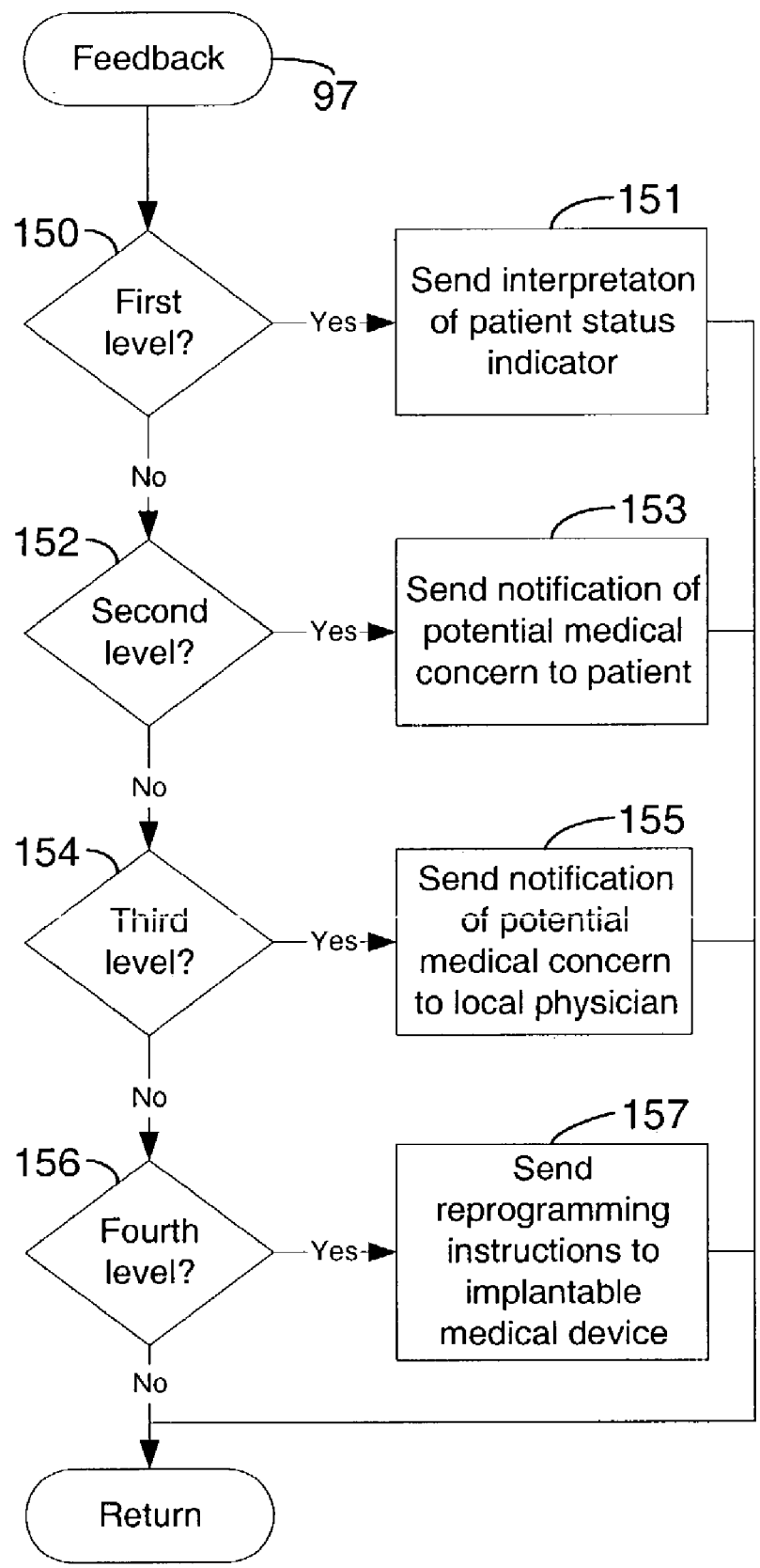
FIG. 11 is a flow diagram showing a routine for providing feedback for use in the method of FIG. 7.

FIG. 11 is a flow diagram showing the routine for providing feedback 97 for use in the method of FIG. 7. The purpose of this routine is to provide tiered feedback based on the patient status indicator. Four levels of feedback are provided with increasing levels of patient involvement and medical care intervention. At a first level (block 150), an interpretation of the patient status indicator 54, preferably phrased in lay terminology, and related health care information is sent to the individual patient (block 151) using the feedback module 55 (shown in FIG. 3). At a second level (block 152), a notification of potential medical concern, based on the analysis and heuristic trends analysis, is sent to the individual patient (block 153) using the feedback module 55. At a third level (block 154), the notification of potential medical concern is forwarded to the physician responsible for the individual patient or similar health care professionals (block 155) using the feedback module 55. Finally, at a fourth level (block 156), reprogramming instructions are sent to the implantable medical device 12 (block 157) using the feedback module 55.

Therefore, through the use of the collected measures sets, the present invention makes possible immediate access to expert medical care at any time and in any place. For example, after establishing and registering for each patient an appropriate baseline set of measures, the database server could contain a virtually up-to-date patient history, which is available to medical providers for the remote diagnosis and prevention of serious illness regardless of the relative location of the patient or time of day.

Moreover, the gathering and storage of multiple sets of critical patient information obtained on a routine basis makes possible treatment methodologies based on an algorithmic analysis of the collected data sets. Each successive introduction of a new collected measures set into the database server would help to continually improve the accuracy and effectiveness of the algorithms used. In addition, the present invention potentially enables the detection, prevention, and cure of previously unknown forms of disorders based on a trends analysis and by a cross-referencing approach to create continuously improving peer-group reference databases.

Finally, the present invention makes possible the provision of tiered patient feedback based on the automated analysis of the collected measures sets. This type of feedback system is suitable for use in, for example, a subscription based health care service. At a basic level, informational feedback can be provided by way of a simple interpretation of the collected data. The feedback could be built up to provide a gradated response to the patient, for example, to notify the patient that he or she is trending into a potential trouble zone. Human interaction could be introduced, both by remotely situated and local medical practitioners. Finally, the feedback could include direct interventive measures, such as remotely reprogramming a patient's IPG.

Figure 12:
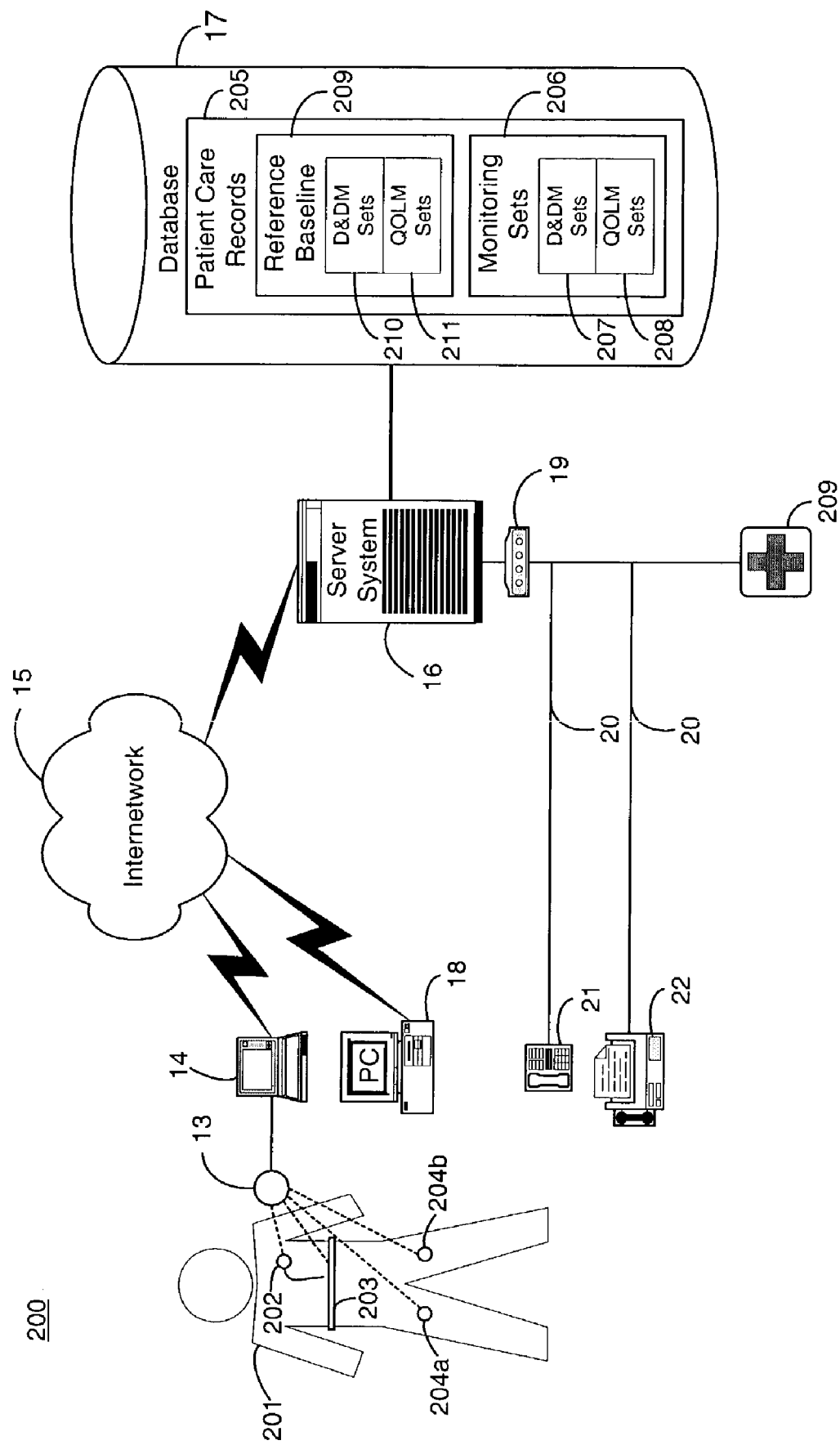
FIG. 12 is a block diagram showing a system for automated collection and analysis of regularly retrieved patient information for remote patient care in accordance with a further embodiment of the present invention.

FIG. 12 is a block diagram showing a system for automated collection and analysis of regularly retrieved patient information for remote patient care 200 in accordance with a further embodiment of the present invention. The system 200 provides remote patient care in a manner similar to the system 10 of FIG. 1, but with additional functionality for diagnosing and monitoring multiple sites within a patient's body using a variety of patient sensors for diagnosing one or more disorder. The patient 201 can be the recipient of an implantable medical device 202, as described above, or have an external medical device 203 attached, such as a Holter monitor-like device for monitoring electrocardiograms. In addition, one or more sites in or around the patient's body can be monitored using multiple sensors 204a, 204b, such as described in U.S. Pat. Nos. 4,987,897; 5,040,536; 5,113,859; and 5,987,352, the disclosures of which are incorporated herein by reference. Other types of devices with physiological measure sensors, both heterogeneous and homogenous, could be used, either within the same device or working in conjunction with each other, as is known in the art.

As part of the system 200, the database 17 stores patient care records 205 for each individual patient to whom remote patient care is being provided. Each patient care record 205 contains normal patient identification and treatment profile information, as well as medical history, medications taken, height and weight, and other pertinent data (not shown). The patient care records 205 consist primarily of monitoring sets 206 storing device and derived measures (D&DM) sets 207 and quality of life and symptom measures (QOLM) sets 208 recorded and determined thereafter on a regular, continuous basis. The organization of the device and derived measures sets 205 for an exemplary cardiac patient care record is described above with reference to FIG. 5. The organization of the quality of life and symptom measures sets 208 is further described below with reference to FIG. 14.

Optionally, the patient care records 205 can further include a reference baseline 209 storing a special set of device and derived reference measures sets 210 and quality of life and symptom measures sets 211 recorded and determined during an initial observation period, such as described in the related, commonly-owned U.S. Pat. No. 6,280,380, issued Aug. 28, 2001, the disclosure of which is incorporated herein by reference. Other forms of database organization are feasible.

Finally, simultaneous notifications can also be delivered to the patient's physician, hospital, or emergency medical services provider 212 using feedback means similar to that used to notify the patient. As described above, the feedback could be by electronic mail or by automated voice mail or facsimile. The feedback can also include normalized voice feedback, such as described in the related, commonly-owned U.S. Pat. No. 6,261,230, issued Jul. 17, 2001, the disclosure of which is incorporated herein by reference.

Figure 13:
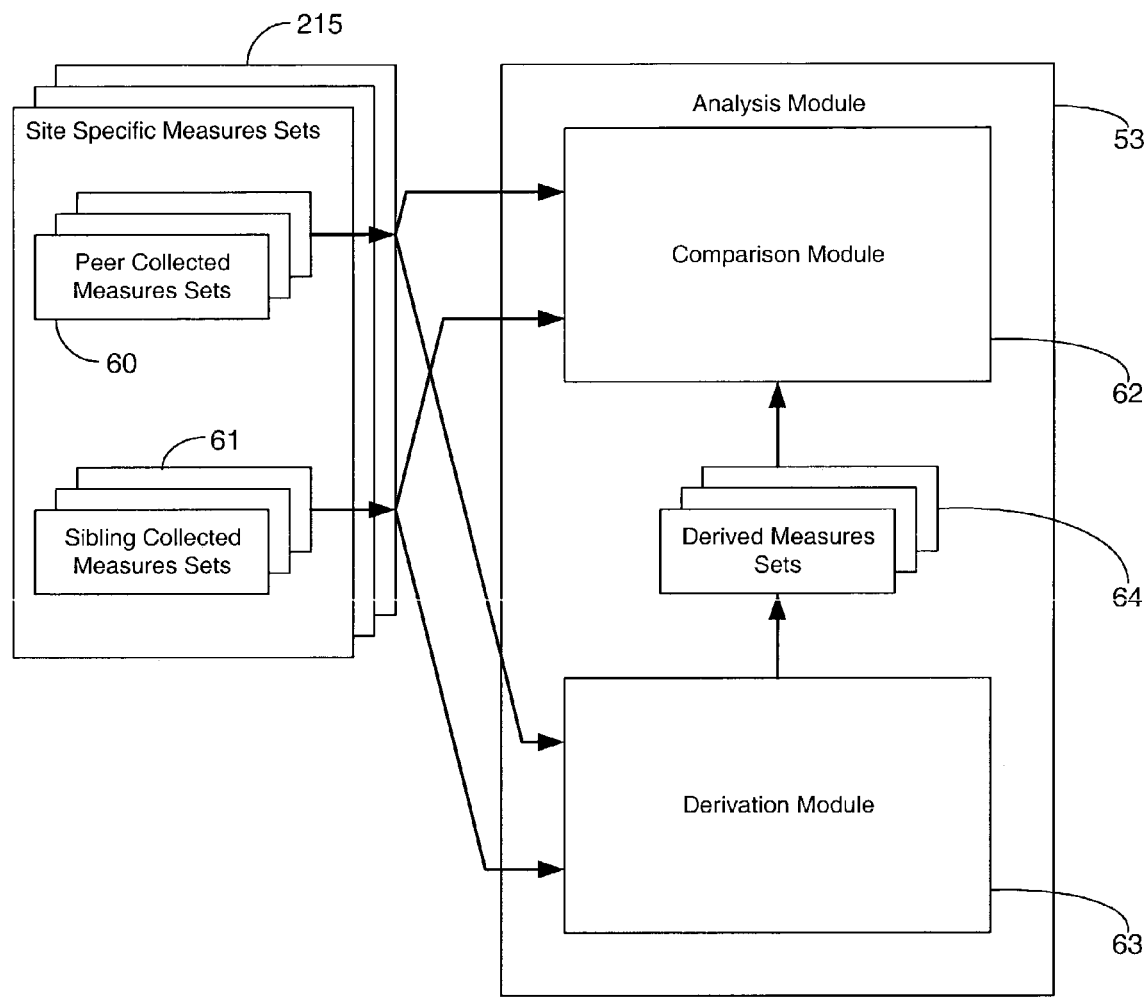
FIG. 13 is a block diagram showing the analysis module of the server system of FIG. 12.

FIG. 13 is a block diagram showing the analysis module 53 of the server system 16 of FIG. 12. The peer collected measures sets 60 and sibling collected measures sets 61 can be organized into site specific groupings based on the sensor from which they originate, that is, implantable medical device 202, external medical device 203, or multiple sensors 204a, 204b. The functionality of the analysis module 53 is augmented to iterate through a plurality of site specific measures sets 215 and one or more disorders.

Figure 14:
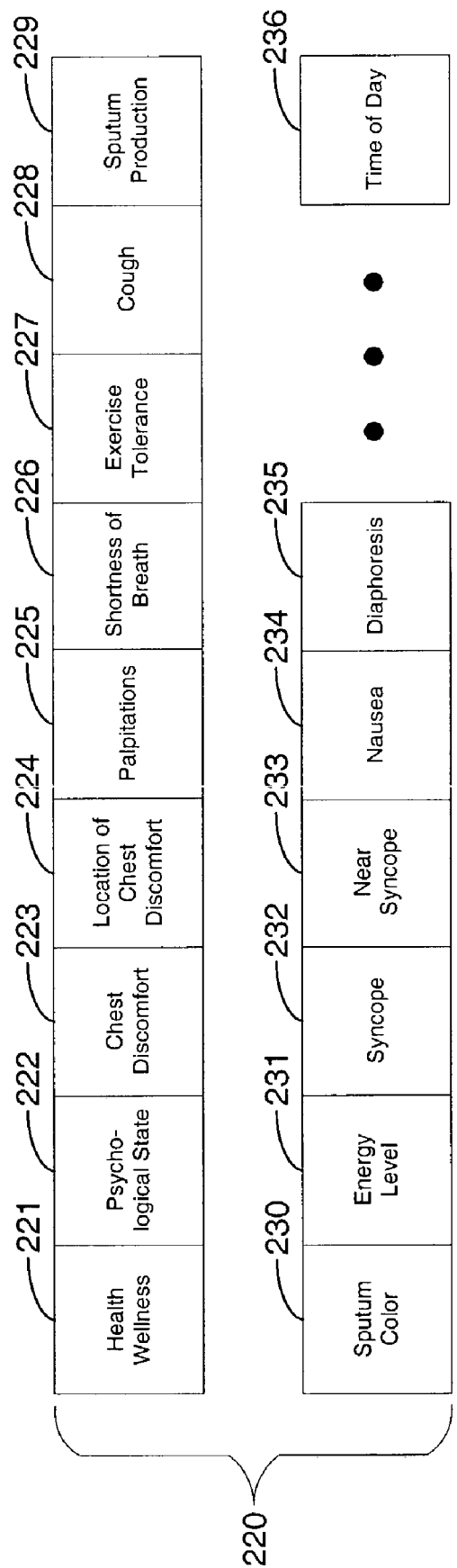
FIG. 14 is a database schema showing, by way of example, the organization of a quality of life and symptom measures set record for care of patients stored as part of a patient care record in the database of the system of FIG. 12.

As an adjunct to remote patient care through the monitoring of measured physiological data via implantable medical device 202, external medical device 203 and multiple sensors 204a, 204b, quality of life and symptom measures sets 208 can also be stored in the database 17 as part of the monitoring sets 206. A quality of life measure is a semi-quantitative self-assessment of an individual patient's physical and emotional well-being and a record of symptoms, such as provided by the Duke Activities Status Indicator. These scoring systems can be provided for use by the patient 11 on the personal computer 18 (shown in FIG. 1) to record his or her quality of life scores for both initial and periodic download to the server system 16. FIG. 14 is a database schema showing, by way of example, the organization of a quality of life and symptom measures set record 220 for care of patients stored as part of a patient care record 205 in the database 17 of the system 200 of FIG. 12. The following exemplary information is recorded for a patient: overall health wellness 221, psychological state 222, chest discomfort 223, location of chest discomfort 224, palpitations 225, shortness of breath 226, exercise tolerance 227, cough 228, sputum production 229, sputum color 230, energy level 231, syncope 232, near syncope 233, nausea 234, diaphoresis 235, time of day 91, and other quality of life and symptom measures as would be known to one skilled in the art.

Other types of quality of life and symptom measures are possible, such as those indicated by responses to the Minnesota Living with Heart Failure Questionnaire described in E. Braunwald, ed., "Heart Disease—A Textbook of Cardiovascular Medicine," pp. 452–454, W. B. Saunders Co. (1997), the disclosure of which is incorporated herein by reference. Similarly, functional classifications based on the relationship between symptoms and the amount of effort required to provoke them can serve as quality of life and symptom measures, such as the New York Heart Association (NYHA) classifications I, II, III and IV, also described in Ibid.

The patient may also add non-device quantitative measures, such as the six-minute walk distance, as complementary data to the device and derived measures sets 207 and the symptoms during the six-minute walk to quality of life and symptom measures sets 208.

FIG. 15 is a record view showing, by way of example, a set of partial cardiac patient care records stored in the database 17 of the system 200 of FIG. 12. Three patient care records are again shown for Patient 1, Patient 2, and Patient 3 with each of these records containing site specific measures sets 215, grouped as follows. First, the patient care record for Patient 1 includes three site specific measures sets A, B and C, corresponding to three sites on Patient 1's body. Similarly, the patient care record for Patient 2 includes two site specific measures sets A and B, corresponding to two sites, both of which are in the same relative positions on Patient 2's body as the sites for Patient 1. Finally, the patient care record for Patient 3 includes two site specific measures sets A and D, also corresponding to two medical device sensors, only one of which, Site A, is in the same relative position as Site A for Patient 1 and Patient 2.

The analysis module 53 (shown in FIG. 13) performs two further forms of comparison in addition to comparing the individual measures for a given patient to other individual measures for that same patient or to other individual measures for a group of other patients sharing the same disease-specific characteristics or to the patient population in general. First, the individual measures corresponding to each body site for an individual patient can be compared to other individual measures for that same patient, a peer group or a general patient population. Again, these comparisons might be peer-to-peer measures projected over time, for instance, comparing measures for each site, A, B and C, for Patient 1, $X_{n_A}$, $X_{n'_A}$, $X_{n''di\ A}$, $X_{n-1_A}$, $X_{n-1'_A}$, $X_{n-1''_A}$, $X_{n-2_A}$, $X_{n-2'_A}$, $X_{n-2''_A}$ ... $X_{0_A}$, $X_{0'_A}$, $X_{0''_A}$; $X_{n_B}$, $X_{n'_B}$, $X_{n''_B}$, $X_{n-1_B}$, $X_{n-1'_B}$, $X_{n-1''_B}$, $X_{n-2_B}$, $X_{n-2'_B}$, $X_{n-2''_B}$ ... $X_{0_B}$, $X_{0'_B}$, $X_{0''_B}$; $X_{n_C}$, $X_{n'_C}$, $X_{n''_C}$, $X_{n-1_C}$, $X_{n-1'_C}$, $X_{n-1''_C}$, $X_{n-2_C}$, $X_{n-2'_C}$, $X_{n-2''_C}$ ... $X_{0_C}$, $X_{0'_C}$, $X_{0''_C}$; comparing comparable measures for Site A for the three patents, $X_{n_A}$, $X_{n'_A}$, $X_{n''_A}$, $X_{n-1_A}$, $X_{n-1'_A}$, $X_{n-1''_A}$, $X_{n-2_A}$, $X_{n-2'_A}$, $X_{n-2''_A}$ ... $X_{0_A}$, $X_{0'_A}$, $X_{0''_A}$; or comparing the individual patient's measures to an average from the group. Similarly, these comparisons might be sibling-to-sibling measures for single snapshots, for instance, comparing comparable measures for Site A for the three patients, $X_{n_A}$, $X_{n'_A}$, $X_{n''_A}$, $Y_{n_A}$, $Y_{n'_A}$, $Y_{n''_A}$, and $Z_{n_A}$, $Z_{n'_A}$, $Z_{n''_A}$, or comparing those same comparable measures for Site A projected over time, for instance, $X_{n_A}$, $X_{n'_A}$, $X_{n''_A}$, $Y_{n_A}$, $Y_{n'_A}$, $Y_{n''_A}$, $Z_{n_A}$, $Z_{n'_A}$, $Z_{n''_A}$, $X_{n-1_A}$, $X_{n-1'_A}$, $X_{n-1''_A}$, $Y_{n-1_A}$, $Y_{n-1'_A}$, $Y_{n-1''_A}$, $Z_{n-1_A}$, $Z_{n-1'_A}$, $Z_{n-1''_A}$, $X_{n-2_A}$, $X_{n-2'_A}$, $X_{n-2''_A}$, $Y_{n-2_A}$, $Y_{n-2'_A}$, $Y_{n-2''_A}$, $Z_{n-2_A}$, $Z_{n-2'_A}$, $Z_{n-2''_A}$ ... $X_{0_A}$, $X_{0'_A}$, $X_{0''_A}$, $Y_{0_A}$, $Y_{0'_A}$, $Y_{0''_A}$, and $Z_{0_A}$, $Z_{0'_A}$, $Z_{0''_A}$. Other forms of site-specific comparisons, including comparisons between individual measures from non-comparable sites between patients, are feasible.

Second, the individual measures can be compared on a disorder specific basis. The individual measures stored in each cardiac patient record can be logically grouped into measures relating to specific disorders and diseases, for instance, congestive heart failure, myocardial infarction, respiratory distress, and atrial fibrillation. The foregoing comparison operations performed by the analysis module 53 are further described below with reference to FIGS. 17A–17B.

Figure 16:
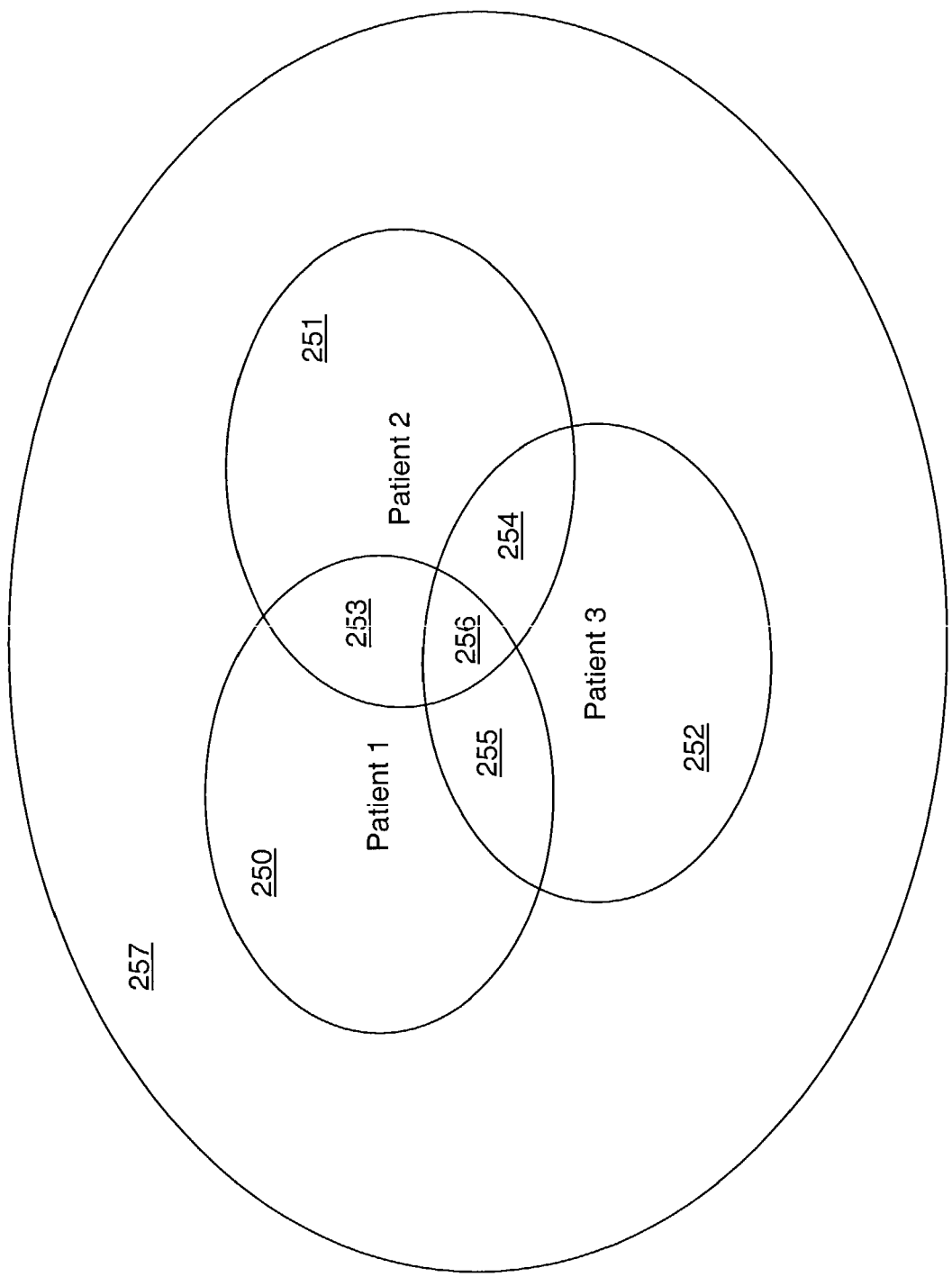
FIG. 16 is a Venn diagram showing, by way of example, peer group overlap between the partial patient care records of FIG. 15.

FIG. 16 is a Venn diagram showing, by way of example, peer group overlap between the partial patient care records 205 of FIG. 15. Each patient care record 205 includes characteristics data 250, 251, 252, including personal traits, demographics, medical history, and related personal data, for patients 1, 2 and 3, respectively. For example, the characteristics data 250 for patient 1 might include personal traits which include gender and age, such as male and an age between 40–45; a demographic of resident of New York City; and a medical history consisting of anterior myocardial infraction, congestive heart failure and diabetes. Similarly, the characteristics data 251 for patient 2 might include identical personal traits, thereby resulting in partial overlap 253 of characteristics data 250 and 251. Similar characteristics overlap 254, 255, 256 can exist between each respective patient. The overall patient population 257 would include the universe of all characteristics data. As the monitoring population grows, the number of patients with personal traits matching those of the monitored patient will grow, increasing the value of peer group referencing. Large peer groups, well matched across all monitored measures, will result in a well known natural history of disease and will allow for more accurate prediction of the clinical course of the patient being monitored. If the population of patients is relatively small, only some traits 256 will be uniformly present in any particular peer group. Eventually, peer groups, for instance, composed of 100 or more patients each, would evolve under conditions in which there would be complete overlap of substantially all salient data, thereby forming a powerful core reference group for any new patient being monitored.

Figure 17A:
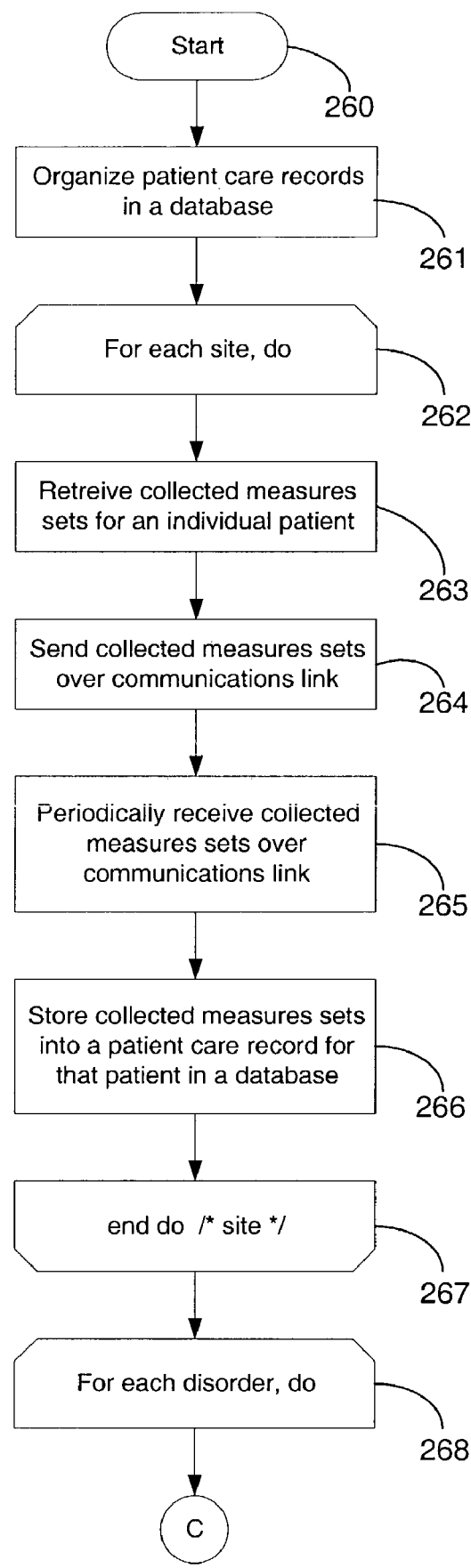
FIGS. 17A–17B are flow diagrams showing a method for automated collection and analysis of regularly retrieved patient information for remote patient care in accordance with a further embodiment of the present invention.
Figure 17B:
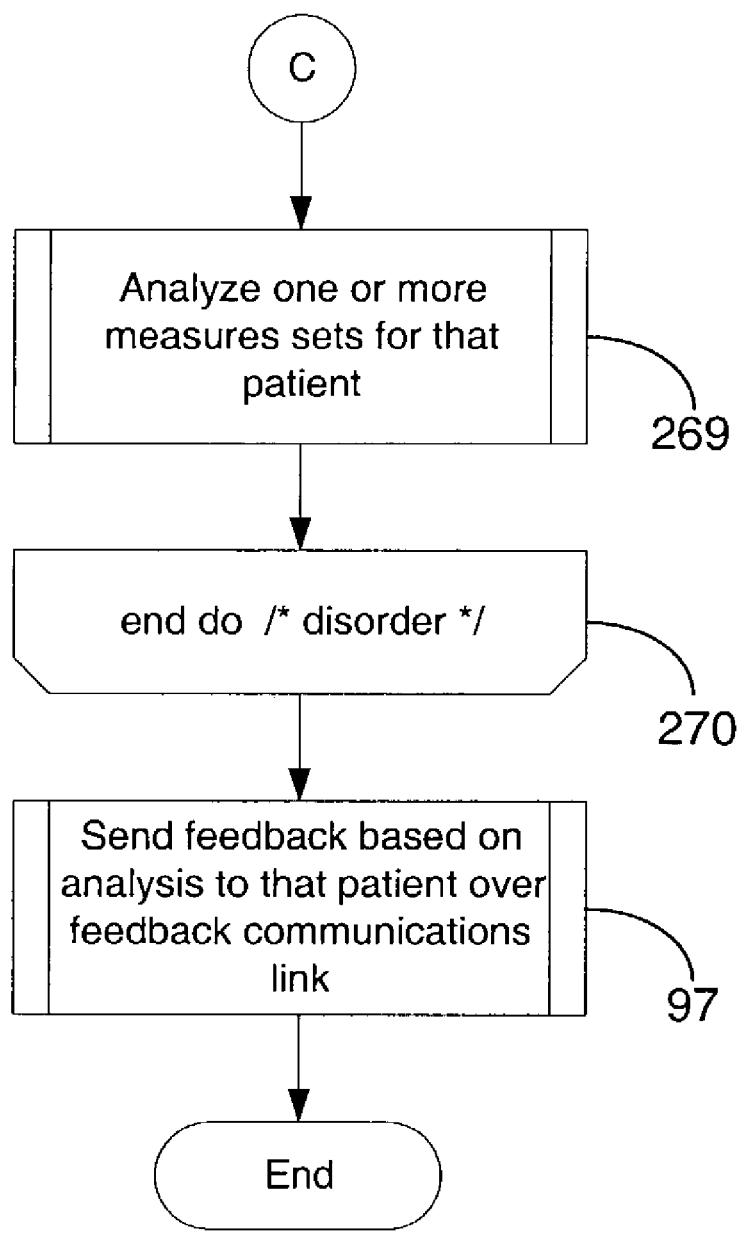

FIGS. 17A–17B are flow diagrams showing a method for automated collection and analysis of regularly retrieved patient information for remote patient care 260 in accordance with a further embodiment of the present invention. As with the method 90 of FIG. 7, this method is also implemented as a conventional computer program and performs the same set of steps as described with reference to FIG. 7 with the following additional functionality. As before, the patient care records are organized in the database 17 with a unique patient care record assigned to each individual patient (block 261). Next, the individual measures for each site are iteratively obtained in a first processing loop (blocks 262–267) and each disorder is iteratively analyzed in a second processing loop (blocks 268–270). Other forms of flow control are feasible, including recursive processing.

During each iteration of the first processing loop (blocks 262–267), the collected measures sets for an individual patient are retrieved from the medical device or sensor located at the current site (block 263) using a programmer, measures sets are sent, on a substantially regular basis, over the internetwork 15 or similar communications link (block 264) and periodically received by the server system 16

(block 265). The collected measures sets are stored into the patient care record 205 in the database 17 for that individual patient (block 266).

During each iteration of the second processing loop (blocks 268–270), one or more of the collected measures sets for that patient are analyzed for the current disorder (block 269), as further described below with reference to FIG. 18. Finally, feedback based on the analysis is sent to that patient over the internetwork 15 as an email message, via telephone line as an automated voice mail or facsimile message, or by similar feedback communications link (block 97), as further described above with reference to FIG. 11.

Figure 18:
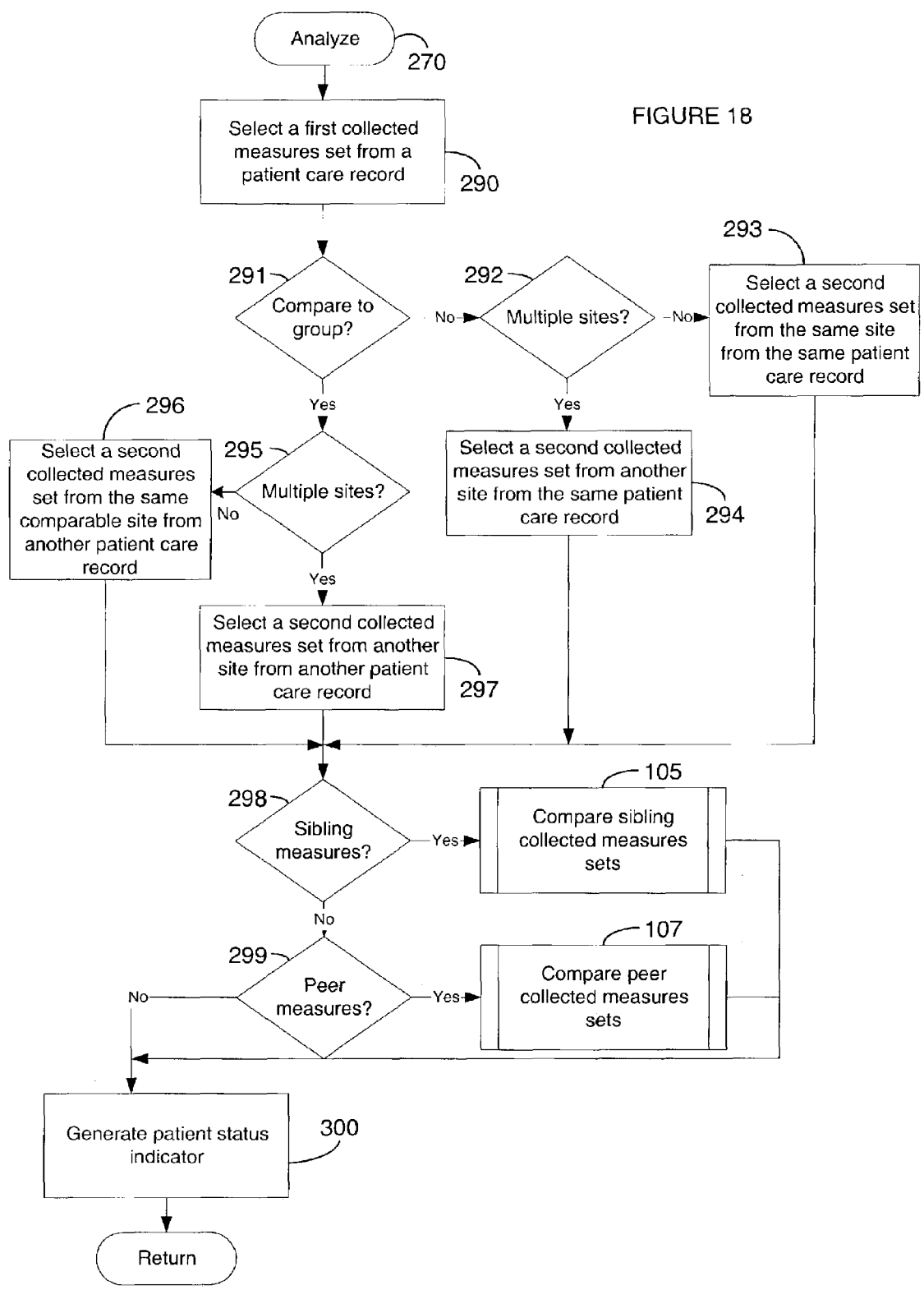
FIG. 18 is a flow diagram showing a routine for analyzing collected measures sets for use in the method of FIGS. 17A–17B.

FIG. 18 is a flow diagram showing a routine for analyzing collected measures sets 270 for use in the method 260 of FIGS. 17A–17B. The purpose of this routine is to make a determination of general patient wellness based on comparisons and heuristic trends analyses of the device and derived measures and quality of life and symptom measures in the patient care records 205 in the database 17. A first collected measures set is selected from a patient care record in the database 17 (block 290). The selected measures set can either be compared to other measures originating from the patient care record for the same individual patient or to measures from a peer group of disease specific patients or for the patient population in general (block 291). If the first collected measures set is being compared within an individual patient care record (block 291), the selected measures set can either be compared to measures from the same site or from another site (block 292). If from the same site (block 292), a second collected measures set is selected for the current site from that patient care record (block 293). Otherwise, a second collected measures set is selected for another site from that patient care record (block 294). Similarly, if the first collected measures set is being compared within a group (block 291), the selected measures set can either be compared to measures from the same comparable site or from another site (block 295). If from the same comparable site (block 295), a second collected measures set is selected for a comparable site from another patient care record (block 296). Otherwise, a second collected measures set is selected for another site from another patient care record (block 297). Note the second collected measures set could also contain averaged measures for a group of disease specific patients or for the patient population in general.

Next, if a sibling measures comparison is to be made (block 298), the routine for comparing sibling collected measures sets is performed (block 105), as further described above with reference to FIG. 9. Similarly, if a peer measures comparison is to be made (block 299), the routine for comparing sibling collected measures sets is performed (block 107), as further described above with reference to FIGS. 10A and 10B.

Finally, a patient status indicator is generated (block 300), as described above with reference to FIG. 8. In addition, the measures sets can be further evaluated and matched to diagnose specific medical disorders, such as congestive heart failure, myocardial infarction, respiratory distress, and atrial fibrillation, as described in related, commonly-owned U.S. Pat. No. 6,336,903, issued Jan. 8, 2002; U.S. Pat. No. 6,368,284, issued Apr. 9, 2002; U.S. Pat. No. 6,398,728, issued Jun. 4, 2002; and U.S. Pat. No. 6,411,840, issued Jun. 25, 2002, the disclosures of which are incorporated herein by reference. In addition, multiple near-simultaneous disorders can be ordered and prioritized as part of the patient status indicator as described in the related, commonly-owned U.S. Pat. No. 6,440,066, issued Aug. 27, 2002, the disclosure of which is incorporated herein by reference.

While the invention has been particularly shown and described as referenced to the embodiments thereof, those skilled in the art will understand that the foregoing and other changes in form and detail may be made therein without departing from the spirit and scope of the invention.

What is claimed is:

1. A system for providing tiered patient feedback for use in automated patient care, comprising:
    a database storing patient care records with each record containing one or more physiological measures regularly recorded by an implantable medical device and relating to individual patient information recorded on a substantially continuous basis;
    an analysis module for providing automated analysis of the physiological measures, each of the physiological measures, each of the physiological measures being representative of at least one of measured and derived patient information retrieved from one such patient care record to determine a patient status;
    a feedback module providing automated tiered feedback to an individual patient responsive to and based on the patient status; and
    a patient programmer for wireless communication with said implantable medical device, the programmer receiving at least some of said automated tiered feedback and for providing automated reprogramming of the implantable medical device by said feedback module.

2. A system according to claim 1, further comprising:
    the feedback module communicating an interpretation of the patient status to the individual patient at a first level of feedback.

3. A system according to claim 1, further comprising:
    the feedback module communicating a notification of potential medical concern based on the patient status to the individual patient at a second level of feedback.

4. A system according to claim 1, further comprising:
    the feedback module communicating a notification of potential medical concern based on the patient status to medical personnel in local proximity to the individual patient at a third level of feedback.

5. A system according to claim 1, further comprising:
    a medical device having a sensor for monitoring and recording the one or more physiological measures; and
    the feedback module communicating a set of reprogramming instructions based on the patient status to the medical device at a fourth level of feedback.

6. A method for providing tiered patient feedback for use in automated patient care, comprising:
    retrieving one or more physiological measures regularly recorded by an implantable medical device and relating to individual patient information recorded on a substantially continuous basis from a patient care record;
    providing automated analysis of the physiological measures, each of the physiological measures being representative of at least one of measured and derived patient information retrieved from one such patient care record to determine a patient status; and
    providing automated tiered feedback to an individual patient responsive to and based on the patient status; and wherein the automated tiered feedback includes wireless automated reprogramming of the implantable medical device based upon the patient status.

7. A method according to claim 6, further comprising: communicating an interpretation of the patient status to the individual patient at a first level of feedback.

8. A method according to claim 6, further comprising: communicating a notification of potential medical concern based on the patient status to the individual patient at a second level of feedback.

9. A method according to claim 6, further comprising: communicating a notification of potential medical concern based on the patient status to medical personnel in local proximity to the individual patient at a third level of feedback.

10. A method according to claim 6, further comprising:

monitoring and recording the one or more physiological measures from a medical device having a sensor; and communicating a set of reprogramming instructions based on the patient status to the medical device at a fourth level of feedback.

11. A computer-readable storage medium holding code for performing the method according to claim 6.

* * * * *

UNITED STATES PATENT AND TRADEMARK OFFICE
CERTIFICATE OF CORRECTION

PATENT NO. : 7,070,562 B2  Page 1 of 1
APPLICATION NO. : 10/422495
DATED : July 4, 2006
INVENTOR(S) : Gust H. Bardy It is certified that error appears in the above-identified patent and that said Letters Patent is hereby corrected as shown below:

Column 18,
Line 14, "an analysis module for providing automated analysis of" should read --an analysis module for providing the automated analysis of--;
Line 15, "the physiological measures, each of the physiological" should read --the physiological--;
Line 24, "said implantable medical device, the programmer" should read --the implantable medical device, the programmer--;
Line 25, "receiving at least some of said automated tiered feed-" should read --receiving at least some of the automated tiered feed- --;
Line 27, "the implantable medical device by said feedback mod-" should read --the implantable medical device by the feedback mod- -- .

Signed and Sealed this

Twelfth Day of December, 2006

JON W. DUDAS
*Director of the United States Patent and Trademark Office*